(12) United States Patent
Bianchi et al.

(10) Patent No.: US 11,337,853 B2
(45) Date of Patent: May 24, 2022

(54) OCULAR IMPLANT DELIVERY DEVICE AND METHOD

(71) Applicant: ForSight Vision4, Inc., Menlo Park, CA (US)

(72) Inventors: Keith Bianchi, Menlo Park, CA (US);
Bill Hartsig, Menlo Park, CA (US);
Scott Nunn, Menlo Park, CA (US);
Mukund Patel, Menlo Park, CA (US);
Mark Sponsel, Menlo Park, CA (US);
Lionel Vedrine, Menlo Park, CA (US);
Ariel Waitz, Menlo Park, CA (US)

(73) Assignee: ForSight Vision4, Inc., South San Francisco, CA (US)

( * ) Notice: Subject to any disclaimer, the term of this patent is extended or adjusted under 35 U.S.C. 154(b) by 315 days.

(21) Appl. No.: 16/380,786

(22) Filed: Apr. 10, 2019

(65) Prior Publication Data
US 2019/0350754 A1     Nov. 21, 2019

Related U.S. Application Data

(63) Continuation of application No. 15/325,995, filed as application No. PCT/US2015/040633 on Jul. 15, 2015, now Pat. No. 10,258,503.
(Continued)

(51) Int. Cl.
*A61F 9/00*     (2006.01)
*A61F 9/007*     (2006.01)
*A61K 9/00*     (2006.01)

(52) U.S. Cl.
CPC ............ *A61F 9/0017* (2013.01); *A61F 9/007* (2013.01); *A61F 9/0026* (2013.01); *A61K 9/0051* (2013.01)

(58) Field of Classification Search
CPC .... A61F 9/0008; A61F 9/0017; A61F 9/0026; A61F 9/007; A61K 9/0051; A61K 31/573; A61K 9/1647; A61K 9/1652; A61P 27/02
See application file for complete search history.

(56) References Cited

U.S. PATENT DOCUMENTS

| 2,564,977 A | 8/1951 | Hu |
| 2,585,815 A | 2/1952 | McLintock |
(Continued)

FOREIGN PATENT DOCUMENTS

| AU | 2015289625 B2 | 10/2019 |
| CN | 102098993 A | 6/2011 |
(Continued)

OTHER PUBLICATIONS

Andrews, "Effect of nonsteroidal anti-inflammatory drugs on LFA-1 and ICAM-1 expression in gastric mucosa," Am J Physiol. Apr. 1994; 266(4 Pt 1):G657-664.
(Continued)

*Primary Examiner* — Quynh-Nhu H. Vu
(74) *Attorney, Agent, or Firm* — Mintz Levin Cohn Ferris Glovsky and Popeo, P.C.

(57) ABSTRACT

An ocular implant system including an ocular implant sized and shaped to be inserted at least partially into an eye; a carrier member with a shell having a central channel extending at least partially through the shell from a proximal end towards a distal end of the shell. A guide sleeve removably attached within at least a first region of the central channel of the shell and defining a proximal port into the central channel that is accessible from the proximal end of the shell. An implant holder removably attached within at least a second region of the central channel of the shell adjacent to a distal end of the guide sleeve and having a pair of graspers adapted to releasably secure the implant at a distal end of the
(Continued)

implant holder. Related devices, systems, and/or methods are described.

25 Claims, 22 Drawing Sheets

Related U.S. Application Data

(60) Provisional application No. 62/024,682, filed on Jul. 15, 2014.

(56) References Cited

U.S. PATENT DOCUMENTS

| | | | |
|---|---|---|---|
| 3,232,117 A | 2/1966 | Gilmont |
| 3,416,530 A | 12/1968 | Ness |
| 3,618,604 A | 11/1971 | Ness |
| 3,641,237 A | 2/1972 | Gould et al. |
| 3,828,777 A | 8/1974 | Ness |
| 3,902,495 A | 9/1975 | Weiss et al. |
| 3,916,899 A | 11/1975 | Theeuwes et al. |
| 3,949,748 A | 4/1976 | Malmin |
| 3,949,750 A | 4/1976 | Freeman |
| 3,961,628 A | 6/1976 | Arnold |
| 3,977,404 A | 8/1976 | Theeuwes |
| 3,995,635 A | 12/1976 | Higuchi et al. |
| 4,008,719 A | 2/1977 | Theeuwes et al. |
| 4,014,333 A | 3/1977 | McIntyre |
| 4,014,334 A | 3/1977 | Theeuwes et al. |
| 4,014,335 A | 3/1977 | Arnold |
| 4,034,756 A | 7/1977 | Higuchi et al. |
| 4,034,758 A | 7/1977 | Theeuwes |
| 4,077,407 A | 3/1978 | Theeuwes et al. |
| 4,111,201 A | 9/1978 | Theeuwes |
| 4,111,203 A | 9/1978 | Theeuwes |
| 4,135,514 A | 1/1979 | Zaffaroni et al. |
| 4,160,452 A | 7/1979 | Theeuwes |
| 4,200,098 A | 4/1980 | Ayer et al. |
| 4,220,152 A | 9/1980 | Dresback |
| 4,220,153 A | 9/1980 | Dresback |
| 4,256,108 A | 3/1981 | Theeuwes |
| 4,298,000 A | 11/1981 | Thill et al. |
| 4,300,557 A | 11/1981 | Refojo et al. |
| 4,309,776 A | 1/1982 | Berguer |
| 4,326,525 A | 4/1982 | Swanson et al. |
| 4,327,725 A | 5/1982 | Cortese et al. |
| 4,439,196 A | 3/1984 | Higuchi |
| 4,475,916 A | 10/1984 | Himmelstein |
| 4,484,922 A | 11/1984 | Rosenwald |
| 4,519,801 A | 5/1985 | Edgren |
| 4,609,374 A | 9/1986 | Ayer |
| 4,627,850 A | 12/1986 | Deters et al. |
| 4,673,405 A | 6/1987 | Guittard et al. |
| 4,693,886 A | 9/1987 | Ayer |
| 4,712,550 A | 12/1987 | Sinnett |
| 4,737,150 A | 4/1988 | Baeumle et al. |
| 4,777,049 A | 10/1988 | Magruder et al. |
| 4,781,675 A | 11/1988 | White |
| 4,863,457 A | 9/1989 | Lee |
| 4,865,846 A | 9/1989 | Kaufman |
| 4,883,459 A | 11/1989 | Calderon |
| 4,959,217 A | 9/1990 | Sanders et al. |
| 5,084,021 A | 1/1992 | Baldwin |
| 5,098,443 A | 3/1992 | Parel et al. |
| 5,128,145 A | 7/1992 | Edgren et al. |
| 5,164,188 A | 11/1992 | Wong |
| 5,174,999 A | 12/1992 | Magruder et al. |
| 5,178,622 A | 1/1993 | Lehner, II |
| 5,277,912 A | 1/1994 | Lowe et al. |
| 5,282,829 A | 2/1994 | Hermes |
| 5,300,114 A | 4/1994 | Gwon et al. |
| 5,322,691 A | 6/1994 | Darougar et al. |
| 5,334,189 A | 8/1994 | Wade |
| 5,336,175 A | 8/1994 | Mames |
| 5,378,475 A | 1/1995 | Smith et al. |
| 5,413,572 A | 5/1995 | Wong et al. |
| 5,443,505 A | 8/1995 | Wong et al. |
| 5,476,511 A | 12/1995 | Gwon et al. |
| 5,516,522 A | 5/1996 | Peyman et al. |
| 5,554,132 A | 9/1996 | Straits et al. |
| 5,562,915 A | 10/1996 | Lowe et al. |
| 5,681,572 A | 10/1997 | Seare, Jr. |
| 5,702,414 A | 12/1997 | Richter et al. |
| 5,766,242 A | 6/1998 | Wong et al. |
| 5,770,076 A | 6/1998 | Chu et al. |
| 5,773,019 A | 6/1998 | Ashton et al. |
| 5,797,898 A | 8/1998 | Santini, Jr. et al. |
| 5,807,581 A | 9/1998 | Rosenblatt et al. |
| 5,824,072 A | 10/1998 | Wong |
| 5,830,173 A | 11/1998 | Avery et al. |
| 5,830,546 A | 11/1998 | Ehret et al. |
| 5,836,935 A | 11/1998 | Ashton et al. |
| 5,868,697 A | 2/1999 | Richter et al. |
| 5,902,598 A | 5/1999 | Chen et al. |
| 5,916,584 A | 6/1999 | O'Donoghue et al. |
| 5,928,662 A | 7/1999 | Phillips |
| 5,951,512 A | 9/1999 | Dalton |
| 5,972,369 A | 10/1999 | Roorda et al. |
| 5,985,328 A | 11/1999 | Chu et al. |
| 6,001,386 A | 12/1999 | Ashton et al. |
| 6,039,712 A | 3/2000 | Fogarty et al. |
| 6,096,070 A | 8/2000 | Ragheb et al. |
| 6,123,861 A | 9/2000 | Santini, Jr. et al. |
| 6,196,993 B1 | 3/2001 | Cohan et al. |
| 6,303,290 B1 | 10/2001 | Liu et al. |
| 6,331,313 B1 | 12/2001 | Wong et al. |
| 6,375,972 B1 | 4/2002 | Guo et al. |
| 6,395,300 B1 | 5/2002 | Straub et al. |
| 6,413,540 B1 | 7/2002 | Yaacobi |
| 6,416,777 B1 | 7/2002 | Yaacobi |
| 6,420,399 B1 | 7/2002 | Graff et al. |
| 6,472,162 B1 | 10/2002 | Coelho et al. |
| 6,605,066 B1 | 8/2003 | Gravagna et al. |
| 6,663,668 B1 | 12/2003 | Chaouk et al. |
| 6,669,950 B2 | 12/2003 | Yaacobi |
| 6,685,940 B2 | 2/2004 | Andya et al. |
| 6,713,081 B2 | 3/2004 | Robinson et al. |
| 6,719,750 B2 | 4/2004 | Varner et al. |
| 6,740,077 B1 | 5/2004 | Brandau et al. |
| 6,756,049 B2 | 6/2004 | Brubaker et al. |
| 6,756,058 B2 | 6/2004 | Brubaker et al. |
| 6,932,983 B1 | 8/2005 | Straub et al. |
| 6,976,982 B2 | 12/2005 | Santini, Jr. et al. |
| 6,986,900 B2 | 1/2006 | Yaacobi |
| 7,026,329 B2 | 4/2006 | Crain et al. |
| 7,074,426 B2 | 7/2006 | Kochinke |
| 7,077,848 B1 | 7/2006 | de Juan, Jr. et al. |
| 7,090,681 B2 | 8/2006 | Weber et al. |
| 7,094,226 B2 | 8/2006 | Yaacobi |
| 7,117,870 B2 | 10/2006 | Prescott |
| 7,141,152 B2 | 11/2006 | Le Febre |
| 7,181,287 B2 | 2/2007 | Greenberg |
| 7,195,774 B2 | 3/2007 | Carvalho et al. |
| 7,195,778 B2 | 3/2007 | Fleshner-Barak et al. |
| 7,211,272 B2 | 5/2007 | Renner et al. |
| 7,252,673 B2 | 8/2007 | Lim |
| 7,276,050 B2 | 10/2007 | Franklin |
| 7,468,065 B2 | 12/2008 | Weber et al. |
| 7,476,510 B2 | 1/2009 | Kapur et al. |
| 7,585,517 B2 | 9/2009 | Cooper et al. |
| 7,615,141 B2 | 11/2009 | Schwartz et al. |
| 7,621,907 B2 | 11/2009 | Rodstrom |
| 7,625,927 B2 | 12/2009 | Klimko et al. |
| 7,678,078 B1 | 3/2010 | Peyman et al. |
| 7,686,016 B2 | 3/2010 | Wharton et al. |
| 7,709,049 B2 | 5/2010 | Chappa |
| 7,753,916 B2 | 7/2010 | Weber et al. |
| 7,883,717 B2 | 2/2011 | Varner et al. |
| 7,893,040 B2 | 2/2011 | Loftsson et al. |
| 7,906,136 B2 | 3/2011 | Wong et al. |
| 7,909,800 B2 | 3/2011 | Cazzini |
| 7,914,442 B1 | 3/2011 | Gazdzinski |
| 7,939,094 B2 | 5/2011 | Schwarz et al. |
| 7,973,068 B2 | 7/2011 | Demopulos et al. |

(56) References Cited

U.S. PATENT DOCUMENTS

| | | |
|---|---|---|
| 8,313,454 B2 | 11/2012 | Yaron et al. |
| 8,399,006 B2 | 3/2013 | de Juan, Jr. et al. |
| 8,403,941 B2 * | 3/2013 | Peterson ............... A61F 2/1678 606/107 |
| 8,623,395 B2 | 1/2014 | de Juan, Jr. et al. |
| 8,905,963 B2 | 12/2014 | de Juan, Jr. et al. |
| 9,987,163 B2 | 6/2018 | Schaller |
| 2002/0026176 A1 | 2/2002 | Varner et al. |
| 2002/0086051 A1 | 7/2002 | Viscasillas |
| 2002/0106395 A1 | 8/2002 | Brubaker |
| 2002/0110591 A1 | 8/2002 | Brubaker et al. |
| 2002/0110592 A1 | 8/2002 | Brubaker et al. |
| 2002/0110635 A1 | 8/2002 | Brubaker et al. |
| 2002/0116009 A1 | 8/2002 | Fraser et al. |
| 2002/0133168 A1 | 9/2002 | Smedley et al. |
| 2003/0003129 A1 | 1/2003 | Yaacobi |
| 2003/0005945 A1 | 1/2003 | Onishi et al. |
| 2003/0014036 A1 | 1/2003 | Varner et al. |
| 2003/0118649 A1 | 6/2003 | Gao et al. |
| 2003/0119177 A1 | 6/2003 | Gruber et al. |
| 2003/0176854 A1 | 9/2003 | Rodstrom |
| 2003/0185872 A1 | 10/2003 | Kochinke |
| 2003/0212383 A1 | 11/2003 | Cote et al. |
| 2003/0235603 A1 | 12/2003 | Schwarz et al. |
| 2004/0011651 A1 | 1/2004 | Becker et al. |
| 2004/0019325 A1 | 1/2004 | Shekalim |
| 2004/0092911 A1 | 5/2004 | Yaacobi |
| 2004/0106906 A1 | 6/2004 | Yaacobi |
| 2004/0131654 A1 | 7/2004 | Yaacobi |
| 2004/0131655 A1 | 7/2004 | Yaacobi |
| 2004/0209359 A1 | 10/2004 | Yayon et al. |
| 2004/0230183 A1 | 11/2004 | Breegi et al. |
| 2004/0238392 A1 | 12/2004 | Peterson et al. |
| 2004/0260380 A1 | 12/2004 | Marco et al. |
| 2004/0260381 A1 | 12/2004 | Marco et al. |
| 2005/0055031 A1 | 3/2005 | Lim |
| 2005/0064010 A1 | 3/2005 | Cooper et al. |
| 2005/0074497 A1 | 4/2005 | Schultz |
| 2005/0112175 A1 | 5/2005 | Yaacobi |
| 2005/0112759 A1 | 5/2005 | Radisic et al. |
| 2005/0113806 A1 | 5/2005 | De Carvalho et al. |
| 2005/0119737 A1 | 6/2005 | Bene et al. |
| 2005/0143363 A1 | 6/2005 | De Juan et al. |
| 2005/0154399 A1 | 7/2005 | Weber et al. |
| 2005/0163711 A1 | 7/2005 | Nycz et al. |
| 2005/0181018 A1 | 8/2005 | Peyman |
| 2005/0244467 A1 | 11/2005 | Nivaggioli et al. |
| 2005/0244469 A1 | 11/2005 | Whitcup et al. |
| 2005/0255144 A1 | 11/2005 | Schultz |
| 2005/0256499 A1 | 11/2005 | Pettis et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0277802 A1 | 12/2005 | Larsen et al. |
| 2005/0281861 A1 | 12/2005 | Hughes et al. |
| 2005/0281863 A1 | 12/2005 | Anderson et al. |
| 2005/0287188 A1 | 12/2005 | Anderson et al. |
| 2006/0013835 A1 | 1/2006 | Anderson et al. |
| 2006/0039952 A1 | 2/2006 | Yaacobi |
| 2006/0052754 A1 | 3/2006 | Fields |
| 2006/0057277 A1 | 3/2006 | Chappa |
| 2006/0073182 A1 | 4/2006 | Wong et al. |
| 2006/0104969 A1 | 5/2006 | Oray et al. |
| 2006/0110428 A1 | 5/2006 | deJuan et al. |
| 2006/0129215 A1 | 6/2006 | Helmus et al. |
| 2006/0154981 A1 | 7/2006 | Klimko et al. |
| 2006/0172941 A1 | 8/2006 | Rastelli et al. |
| 2006/0182783 A1 | 8/2006 | Hughes et al. |
| 2006/0200097 A1 | 9/2006 | Humayun et al. |
| 2006/0233858 A1 | 10/2006 | Tzekov et al. |
| 2006/0246112 A1 | 11/2006 | Snyder et al. |
| 2006/0257450 A1 | 11/2006 | Mudumba et al. |
| 2006/0258000 A1 | 11/2006 | Allen et al. |
| 2006/0258994 A1 | 11/2006 | Avery |
| 2006/0276738 A1 | 12/2006 | Becker |
| 2007/0020336 A1 | 1/2007 | Loftsson et al. |
| 2007/0021357 A1 | 1/2007 | Tobia et al. |
| 2007/0026037 A1 | 2/2007 | Kloke et al. |
| 2007/0059336 A1 | 3/2007 | Hughes et al. |
| 2007/0071756 A1 | 3/2007 | Peyman |
| 2007/0072933 A1 | 3/2007 | Peyman |
| 2007/0077270 A1 | 4/2007 | Wen |
| 2007/0088414 A1 | 4/2007 | Campbell et al. |
| 2007/0119450 A1 | 5/2007 | Wharton et al. |
| 2007/0128644 A1 | 6/2007 | Munenaka |
| 2007/0131610 A1 | 6/2007 | Peng et al. |
| 2007/0131611 A1 | 6/2007 | Peng et al. |
| 2007/0134305 A1 | 6/2007 | Zilberman |
| 2007/0141111 A1 | 6/2007 | Suokas et al. |
| 2007/0191863 A1 | 8/2007 | De Juan et al. |
| 2007/0197491 A1 | 8/2007 | Robin et al. |
| 2007/0203174 A1 | 8/2007 | Klimko et al. |
| 2007/0212397 A1 | 9/2007 | Roth |
| 2007/0233037 A1 | 10/2007 | Gifford et al. |
| 2007/0235331 A1 | 10/2007 | Simpson et al. |
| 2007/0243230 A1 | 10/2007 | de Juan et al. |
| 2007/0260201 A1 | 11/2007 | Prausnitz et al. |
| 2007/0269487 A1 | 11/2007 | de Juan et al. |
| 2008/0003219 A1 | 1/2008 | Peyman |
| 2008/0004329 A1 | 1/2008 | Jamieson et al. |
| 2008/0020045 A1 | 1/2008 | Chappa et al. |
| 2008/0038316 A1 | 2/2008 | Wong et al. |
| 2008/0057561 A1 | 3/2008 | Takahashi et al. |
| 2008/0066739 A1 | 3/2008 | LeMahieu et al. |
| 2008/0066741 A1 | 3/2008 | LeMahieu et al. |
| 2008/0069854 A1 | 3/2008 | Xiao et al. |
| 2008/0089923 A1 | 4/2008 | Burkstrand et al. |
| 2008/0097459 A1 * | 4/2008 | Kammerlander ..... A61F 2/1664 606/107 |
| 2008/0111282 A1 | 5/2008 | Xie et al. |
| 2008/0124372 A1 | 5/2008 | Hossainy et al. |
| 2008/0139674 A1 | 6/2008 | Archambeau et al. |
| 2008/0145406 A1 | 6/2008 | Asgharian et al. |
| 2008/0146679 A1 | 6/2008 | Archambeau et al. |
| 2008/0147021 A1 | 6/2008 | Jani |
| 2008/0152694 A1 | 6/2008 | Lobl et al. |
| 2008/0154241 A1 | 6/2008 | Burkstrand et al. |
| 2008/0161741 A1 | 7/2008 | Bene et al. |
| 2008/0167600 A1 | 7/2008 | Peyman |
| 2008/0172014 A1 | 7/2008 | Whitcup et al. |
| 2008/0181930 A1 | 7/2008 | Rodstrom et al. |
| 2008/0200922 A1 | 8/2008 | Brown |
| 2008/0207502 A1 | 8/2008 | Rastelli et al. |
| 2008/0213611 A1 | 9/2008 | Asgari |
| 2008/0216736 A1 | 9/2008 | David |
| 2008/0228127 A1 | 9/2008 | Burns et al. |
| 2008/0233053 A1 | 9/2008 | Gross et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0241219 A1 | 10/2008 | Whitcup et al. |
| 2008/0241220 A1 | 10/2008 | Whitcup et al. |
| 2008/0241221 A1 | 10/2008 | Whitcup et al. |
| 2008/0241222 A1 | 10/2008 | Whitcup et al. |
| 2008/0241223 A1 | 10/2008 | Nivaggioli et al. |
| 2008/0249501 A1 | 10/2008 | Yamasaki |
| 2008/0286338 A1 | 11/2008 | Rosenthal et al. |
| 2008/0292679 A1 | 11/2008 | Lyons et al. |
| 2009/0005864 A1 | 1/2009 | Eggleston |
| 2009/0036827 A1 | 2/2009 | Cazzini |
| 2009/0043253 A1 | 2/2009 | Podaima |
| 2009/0047335 A1 | 2/2009 | Rastelli et al. |
| 2009/0082631 A1 | 3/2009 | Cronin et al. |
| 2009/0087494 A1 | 4/2009 | Kompella et al. |
| 2009/0092654 A1 | 4/2009 | de Juan, Jr. et al. |
| 2009/0093752 A1 | 4/2009 | Richard et al. |
| 2009/0099626 A1 | 4/2009 | de Juan, Jr. et al. |
| 2009/0104243 A1 | 4/2009 | Utkhede et al. |
| 2009/0105749 A1 | 4/2009 | de Juan et al. |
| 2009/0124997 A1 | 5/2009 | Pettis et al. |
| 2009/0214601 A1 | 8/2009 | Chappa et al. |
| 2009/0224064 A1 | 9/2009 | Brodbeck et al. |
| 2009/0234449 A1 | 9/2009 | De Juan, Jr. et al. |
| 2009/0240215 A1 | 9/2009 | Humayun et al. |

(56) References Cited

U.S. PATENT DOCUMENTS

| | | |
|---|---|---|
| 2009/0247458 A1 | 10/2009 | Watson et al. |
| 2009/0258069 A1 | 10/2009 | Burnier et al. |
| 2009/0263346 A1 | 10/2009 | Taft et al. |
| 2009/0263495 A1 | 10/2009 | Watson et al. |
| 2009/0274730 A1 | 11/2009 | Watson et al. |
| 2009/0274771 A1 | 11/2009 | Watson et al. |
| 2009/0280470 A1 | 11/2009 | Fare et al. |
| 2009/0281621 A1 | 11/2009 | Becker |
| 2009/0324686 A1 | 12/2009 | Cooper et al. |
| 2009/0324687 A1 | 12/2009 | Cooper et al. |
| 2009/0324688 A1 | 12/2009 | Cooper et al. |
| 2009/0324689 A1 | 12/2009 | Cooper et al. |
| 2009/0324690 A1 | 12/2009 | Cooper et al. |
| 2009/0326448 A1 | 12/2009 | Huo et al. |
| 2010/0003333 A1 | 1/2010 | Watson et al. |
| 2010/0004189 A1 | 1/2010 | Watson et al. |
| 2010/0008997 A1 | 1/2010 | Watson et al. |
| 2010/0009008 A1 | 1/2010 | Watson et al. |
| 2010/0010452 A1 | 1/2010 | Paques et al. |
| 2010/0011888 A1 | 1/2010 | Pawliszyn et al. |
| 2010/0015157 A1 | 1/2010 | Andya et al. |
| 2010/0016786 A1 | 1/2010 | Drews et al. |
| 2010/0021464 A1 | 1/2010 | Archambeau et al. |
| 2010/0022943 A1 | 1/2010 | Mauch et al. |
| 2010/0022945 A1 | 1/2010 | Rodstrom |
| 2010/0023033 A1 | 1/2010 | Mauch et al. |
| 2010/0028442 A1 | 2/2010 | Archambeau et al. |
| 2010/0028443 A1 | 2/2010 | Watson et al. |
| 2010/0030136 A1 | 2/2010 | Dacquay et al. |
| 2010/0034870 A1 | 2/2010 | Sim et al. |
| 2010/0083963 A1 | 4/2010 | Wharton et al. |
| 2010/0100054 A1 | 4/2010 | Cormier et al. |
| 2010/0100104 A1 | 4/2010 | Yu et al. |
| 2010/0114017 A1 | 5/2010 | Lenker et al. |
| 2010/0114309 A1 | 5/2010 | de Juan, Jr. et al. |
| 2010/0168535 A1 | 7/2010 | Robinson et al. |
| 2010/0174272 A1 | 7/2010 | Weiner |
| 2010/0185205 A1 | 7/2010 | Novakovic et al. |
| 2010/0197512 A1 | 8/2010 | Trinkle et al. |
| 2010/0216702 A1 | 8/2010 | Szkudlinski et al. |
| 2010/0221309 A1 | 9/2010 | Myers et al. |
| 2010/0241102 A1 | 9/2010 | Ma |
| 2010/0255061 A1 | 10/2010 | de Juan, Jr. et al. |
| 2010/0256597 A1 | 10/2010 | Prausnitz et al. |
| 2010/0266664 A1 | 10/2010 | Asgharian et al. |
| 2010/0286121 A1 | 11/2010 | Rohrs et al. |
| 2010/0286791 A1 | 11/2010 | Goldsmith |
| 2010/0297046 A1 | 11/2010 | Schwartz et al. |
| 2010/0297120 A1 | 11/2010 | Beliveau et al. |
| 2010/0297193 A1 | 11/2010 | Archambeau et al. |
| 2010/0303917 A1 | 12/2010 | Watson et al. |
| 2010/0303918 A1 | 12/2010 | Watson et al. |
| 2010/0310664 A1 | 12/2010 | Watson et al. |
| 2010/0310665 A1 | 12/2010 | Watson et al. |
| 2010/0316723 A1 | 12/2010 | Watson et al. |
| 2010/0330146 A1 | 12/2010 | Chauhan et al. |
| 2011/0009571 A1 | 1/2011 | Taft et al. |
| 2011/0014264 A1 | 1/2011 | Helmus et al. |
| 2011/0033933 A1 | 2/2011 | Gharib et al. |
| 2011/0034448 A1 | 2/2011 | Chang et al. |
| 2011/0081384 A1 | 4/2011 | Archambeau et al. |
| 2011/0098686 A1 | 4/2011 | Varner et al. |
| 2011/0104155 A1 | 5/2011 | Rekik |
| 2011/0108025 A1 | 5/2011 | Fink et al. |
| 2011/0111006 A1 | 5/2011 | Wong et al. |
| 2011/0112188 A1 | 5/2011 | Tobia et al. |
| 2011/0117083 A1 | 5/2011 | Bais et al. |
| 2011/0125178 A1 | 5/2011 | Drews et al. |
| 2011/0159073 A1 | 6/2011 | deJuan et al. |
| 2011/0196317 A1 | 8/2011 | Lust et al. |
| 2011/0206646 A1 | 8/2011 | Alfonso et al. |
| 2012/0029445 A1 | 2/2012 | de Juan, Jr. et al. |
| 2012/0029470 A1 | 2/2012 | de Juan, Jr. et al. |
| 2012/0245505 A1 | 9/2012 | Robinson et al. |
| 2013/0204209 A1 | 8/2013 | de Juan, Jr. et al. |
| 2013/0218081 A1 | 8/2013 | Roth |
| 2013/0274691 A1 | 10/2013 | de Juan, Jr. et al. |
| 2013/0274692 A1 | 10/2013 | Alster et al. |
| 2013/0324918 A1 | 12/2013 | de Juan, Jr. et al. |
| 2013/0324942 A1 | 12/2013 | de Juan, Jr. et al. |
| 2014/0031769 A1 | 1/2014 | de Juan, Jr. et al. |
| 2014/0033800 A1 | 2/2014 | Farinas et al. |
| 2014/0073714 A1 | 3/2014 | Reich et al. |
| 2014/0114323 A1* | 4/2014 | Kudo .................. A61F 9/0017 606/107 |
| 2014/0121609 A1 | 5/2014 | de Juan, Jr. et al. |
| 2014/0221941 A1 | 8/2014 | Erickson et al. |
| 2014/0243795 A1 | 8/2014 | Varner et al. |
| 2014/0276482 A1 | 9/2014 | Astafieva et al. |
| 2014/0276901 A1* | 9/2014 | Auld .................... A61F 2/1678 606/107 |
| 2014/0296800 A1 | 10/2014 | Erickson et al. |
| 2014/0303637 A1* | 10/2014 | Downer ............... A61F 2/1672 606/107 |
| 2014/0326249 A1 | 11/2014 | Cappiello et al. |
| 2014/0358125 A1 | 12/2014 | de Juan, Jr. et al. |
| 2014/0379079 A1 | 12/2014 | Ben Nun |
| 2015/0045805 A1 | 2/2015 | Kontur et al. |
| 2015/0080846 A1 | 3/2015 | de Juan, Jr. et al. |
| 2015/0250647 A1 | 9/2015 | de Juan, Jr. et al. |
| 2015/0297402 A1 | 10/2015 | de Juan, Jr. et al. |
| 2016/0038488 A1 | 2/2016 | Horvath et al. |
| 2016/0101046 A1 | 4/2016 | Reich et al. |
| 2016/0128867 A1 | 5/2016 | Bachelder et al. |
| 2016/0184134 A1 | 6/2016 | Varner et al. |
| 2016/0258855 A1 | 9/2016 | Farinas et al. |
| 2016/0302965 A1 | 10/2016 | Erickson et al. |
| 2017/0165108 A1 | 6/2017 | Bianchi et al. |
| 2017/0165110 A1 | 6/2017 | Erickson et al. |
| 2017/0172794 A1 | 6/2017 | Varner et al. |
| 2017/0258634 A1 | 9/2017 | de Juan, Jr. et al. |
| 2018/0147204 A1 | 5/2018 | Horvath et al. |
| 2018/0161202 A1 | 6/2018 | de Juan, Jr. et al. |
| 2018/0243130 A1 | 8/2018 | Doud et al. |
| 2018/0243131 A1 | 8/2018 | Erickson et al. |
| 2018/0289542 A1 | 10/2018 | de Juan, Jr. et al. |
| 2018/0292403 A1 | 10/2018 | de Juan, Jr. et al. |
| 2019/0117454 A1 | 4/2019 | Campbell et al. |
| 2019/0336335 A1 | 11/2019 | de Juan, Jr. et al. |
| 2019/0365757 A1 | 12/2019 | Horvath et al. |
| 2020/0030142 A1 | 1/2020 | Erickson et al. |
| 2020/0060874 A1 | 2/2020 | Bachelder et al. |
| 2020/0107955 A1 | 4/2020 | Erickson et al. |

FOREIGN PATENT DOCUMENTS

| | | |
|---|---|---|
| CN | 102365109 A | 2/2012 |
| EP | 0228185 B1 | 7/1990 |
| EP | 0498471 A2 | 8/1992 |
| EP | 0500143 A2 | 8/1992 |
| EP | 0671165 A2 | 9/1995 |
| EP | 0295248 B2 | 4/1999 |
| EP | 0944658 B1 | 6/2003 |
| EP | 1671624 A1 | 6/2006 |
| EP | 1385452 B1 | 9/2006 |
| EP | 1409065 B1 | 1/2007 |
| EP | 1337284 B1 | 12/2007 |
| EP | 1911481 | 4/2008 |
| EP | 1521572 B1 | 3/2009 |
| EP | 3169289 B1 | 4/2020 |
| EP | 3679908 A1 | 7/2020 |
| JP | 2004525695 A | 8/2004 |
| JP | 2006526462 A | 11/2006 |
| RU | 2387462 C2 | 4/2010 |
| WO | WO-88/04573 A1 | 6/1988 |
| WO | WO-90/07545 A2 | 7/1990 |
| WO | WO-95/28984 A1 | 11/1995 |
| WO | WO-97/29850 | 8/1997 |
| WO | WO-98/25982 | 6/1998 |
| WO | WO-00/48660 | 8/2000 |
| WO | WO-01/26714 | 4/2001 |
| WO | WO-01/50943 | 7/2001 |
| WO | WO-03/077972 | 9/2003 |
| WO | WO-03/082188 | 10/2003 |

(56) References Cited

FOREIGN PATENT DOCUMENTS

| | | |
|---|---|---|
| WO | WO-2004/000267 | 12/2003 |
| WO | WO-2004/112653 | 12/2004 |
| WO | WO-2005/016401 | 2/2005 |
| WO | WO-2005/027906 | 3/2005 |
| WO | WO-2005/028006 | 3/2005 |
| WO | WO-2005/091922 | 10/2005 |
| WO | WO-2005/107705 | 11/2005 |
| WO | WO-2005/110362 | 11/2005 |
| WO | WO-2005/110436 | 11/2005 |
| WO | WO-2005/110473 | 11/2005 |
| WO | WO-2005/117780 A2 | 12/2005 |
| WO | WO-2006/014484 | 2/2006 |
| WO | WO-2006/015385 | 2/2006 |
| WO | WO-2006/023530 | 3/2006 |
| WO | WO-2006/031358 | 3/2006 |
| WO | WO-2006/031388 | 3/2006 |
| WO | WO-2006/044614 | 4/2006 |
| WO | WO-2006/068838 | 6/2006 |
| WO | WO-2006/071554 | 7/2006 |
| WO | WO-2006/082588 | 8/2006 |
| WO | WO-2006/108054 | 10/2006 |
| WO | WO-2006/125106 A1 | 11/2006 |
| WO | WO-2006/127962 | 11/2006 |
| WO | WO-2006/138609 | 12/2006 |
| WO | WO-2007/012974 | 2/2007 |
| WO | WO-2007/035621 | 3/2007 |
| WO | WO-2007/038453 | 4/2007 |
| WO | WO-2007/044534 | 4/2007 |
| WO | WO-2007/047744 | 4/2007 |
| WO | WO-2007//066339 | 6/2007 |
| WO | WO-2007/084582 | 7/2007 |
| WO | WO-2007/084765 | 7/2007 |
| WO | WO-2007/101204 | 9/2007 |
| WO | WO-2007/117394 | 10/2007 |
| WO | WO-2007/131050 | 11/2007 |
| WO | WO-2007/133761 | 11/2007 |
| WO | WO-2007/133762 | 11/2007 |
| WO | WO-2008/003043 | 1/2008 |
| WO | WO-2008/005240 | 1/2008 |
| WO | WO-2008/011125 | 1/2008 |
| WO | WO-2008/019265 A2 | 2/2008 |
| WO | WO-2008/033924 | 3/2008 |
| WO | WO-2008/040062 | 4/2008 |
| WO | WO-2008/045272 | 4/2008 |
| WO | WO-2008/052145 | 5/2008 |
| WO | WO-2008/060359 | 5/2008 |
| WO | WO-2008//061043 A2 | 5/2008 |
| WO | WO-2008/076544 | 6/2008 |
| WO | WO-2008/084063 A1 | 7/2008 |
| WO | WO-2008/094989 | 8/2008 |
| WO | WO-2008/115290 | 9/2008 |
| WO | WO-2008/116165 | 9/2008 |
| WO | WO-2008/144340 | 11/2008 |
| WO | WO-2008/144919 | 12/2008 |
| WO | WO-2009/012075 | 1/2009 |
| WO | WO-2009/023615 | 2/2009 |
| WO | WO-2009/046164 | 4/2009 |
| WO | WO-2009/055620 | 4/2009 |
| WO | WO-2009/055671 | 4/2009 |
| WO | WO-2009/055729 | 4/2009 |
| WO | WO-2009/055824 | 4/2009 |
| WO | WO-2009/061607 | 5/2009 |
| WO | WO-2009/073192 | 6/2009 |
| WO | WO-2009/086112 | 7/2009 |
| WO | WO-2009/089409 | 7/2009 |
| WO | WO-2009/094466 | 7/2009 |
| WO | WO-2009/112878 | 9/2009 |
| WO | WO-2009/117112 | 9/2009 |
| WO | WO-2009/124096 | 10/2009 |
| WO | WO-2009/128932 | 10/2009 |
| WO | WO-2009/134929 | 11/2009 |
| WO | WO-2009/137777 | 11/2009 |
| WO | WO-2010/008424 | 1/2010 |
| WO | WO-2010/021993 | 2/2010 |
| WO | WO-2010/047753 | 4/2010 |
| WO | WO-2010/062628 | 6/2010 |
| WO | WO-2010/066714 | 6/2010 |
| WO | WO-2010//075565 A2 | 7/2010 |
| WO | WO-2010/078063 | 7/2010 |
| WO | WO-2010/080987 A2 | 7/2010 |
| WO | WO-2010/088548 | 8/2010 |
| WO | WO-2010/093945 | 8/2010 |
| WO | WO-2010/095940 | 8/2010 |
| WO | WO-2010/125416 | 11/2010 |
| WO | WO-2010/126908 | 11/2010 |
| WO | WO-2010/135369 | 11/2010 |
| WO | WO-2010//141729 | 12/2010 |
| WO | WO-2010/147661 | 12/2010 |
| WO | WO-2011/008896 | 1/2011 |
| WO | WO-2011/008897 | 1/2011 |
| WO | WO-2011/028850 | 3/2011 |
| WO | WO-2011/034627 | 3/2011 |
| WO | 2011075481 A1 | 6/2011 |
| WO | WO-2011/079232 | 6/2011 |
| WO | WO-2012/019136 | 2/2012 |
| WO | WO-2013/082452 A1 | 6/2013 |
| WO | WO-2013/116061 A1 | 8/2013 |
| WO | 2013184727 A1 | 12/2013 |
| WO | 2014165345 A1 | 10/2014 |
| WO | 2016011191 A1 | 1/2016 |
| WO | WO-2017/087902 A1 | 5/2017 |

OTHER PUBLICATIONS

Avery et al., "Intravitreal bevacizumab (Avastin) in the treatment of proliferative diabetic retinopathy," Ophthalmology. Oct. 2006, 113(10):1695-1705.e6.

Bakri et al., "The effect of intravitreal triamcinolone acetonide on intraocular pressure," Ophthalmic Surgery, Lasers and Imaging, Sep./Oct. 2003;34(5): 386-390.

Bird et al., Transport Phenomena, John Wiley & Sons, Inc., New York, 1960, pp. 196-201.

Block et al., "Solubility and dissolution of triamcinolone acetonide," Journal of Pharmaceutical Sciences, Apr. 1973; 62(4):617-621.

Castro et al., "Effect of COX inhibitors on VEGF-induced retinal vascular leakage and experimental corneal and choroidal neovascularization," Exp Eye Res. Aug. 2004;79(2):275-285.

Chirila et al., "The Vitreous Humor" in *Handbook of Biomaterial Properties*, eds. Black & Hastings. Chapman & Hall, London, 1998; pp. 125-131.

Cousins et al., "Program# 1251—Targeting Complement Factors 5 in Combination with Vascular Endothelial Growth Factor (VEGF) Inhibition for Neovascular Age Related Macular Degeneration (AMD): Results of a Phase 1 Study," [Presentation Abstract], AMD Clinical Trials Session # 220, May 3, 2010. 2 pages.

Deissler et al., "VEGF-induced effects on proliferation, migration and tight junctions are restored by ranibizumab (Lucentis) in microvascular retinal endothelial cells,"Br J Ophthalmol 2008;92:839-843.

Donoso et al., "The role of inflammation in the pathogenesis of age-related macular degeneration," Surv Ophthalmol. Mar.-Apr. 2006;51(2):137-52.

Edelhauser, H et al. "Ophthalmic Drug Delivery Systems for the Treatment of Retinal Diseases Basic Research to Clinical Applications." Investigative Ophthalmology & Visual Science, Nov. 2010. vol. 51, No. 11. pp. 5403-5420.

European Medicine Agency, Scientific Discussion; retrieved from the Internet; <http://www.ema.europa.eu/docs/en_GB/document_library/EPAR_-_Scientific_Discussion/human/000715/WC500043550.pdf>, EMEA 2007, 54 pages total. 2007.

Funatsu et al. "Association of vitreous inflammatory factors with diabetic macular edema," Ophthalmology 2009;116:73-79.

Gaudreault et al., "Preclinical Pharmacokinetics of Ranibizumab (rhuFabV2) after a Single Intravitreal Administration," Investigative Ophthalmology and Visual Science. 2005;46:726-733. Retrieved from the Internet: <<http://www.iovs.org/cgi/reprint/46/2/726>>.

Gillies et al., "Intravitreal triamcinolone for refractory diabetic macular edema: two-year results of a double-masked, placebo-controlled, randomized clinical trial," Ophthalmology. Sep. 2006;113(9):1533-1538.

(56) References Cited

OTHER PUBLICATIONS

Hastedt & Wright, "Diffusion in porous materials above the percolation threshold," Pharm. Res. Sep. 1990; 7(9):893-901 (1990).

Heier et al., "Ketorolac versus prednisolone versus combination therapy in the treatment of acute pseudophakic cystoid macular edema," Ophthalmology. Nov. 2000;107(11):2034-2038; discussion 2039.

Jena et al., "A Novel Technique for Surface Area and Particle Size Determination of Components of Fuel Cells and Batteries," Porous Materials, Inc., Dec. 2006, 3 pages total. Downloaded from the Internet: <<http://www.pmiapp.com/publications/docs/A_Novel_technique_for_surface_area.pdf>>.

Kang et al., "Inhibitory effects of anti-inflammatory drugs on interleukin-6 bioactivity," Biol Pharm Bull. Jun. 2001;24(6):701-703.

Lopez-Armada et al., "Modulation of cell recruitment by anti-inflammatory agents in antigen-induced arthritis," Ann Rheum Dis Nov. 2002;61(11):1027-1030.

Luncentis, INN-Ranibizumab, "Scientific Discussion," European Medicines Agency; retrieved from the Internet:<http://www.ema.europa.eu/docs/en_GB/document_library/EPAR_-_Assessment_Report_-_Variation/human/000715/WC500101009.pdf>. Oct. 21, 2010. 32 pages.

Metal Powder Industries Federation, Porous Metal Design Guidebook, 2007, 24 pages total. Downloaded from the Internet: <<http://www.mpif.org/DesignCenter/porous.pdf>>.

MOTT Corporation, "Sintered Metal Powder Media," American Filtration & Separation Society 2007, 2 pages total. Downloaded from the Internet:<<http://www.afssociety.org/education/0907oneminute.htm>>.

Navarro, "The Optical Design of the Human Eye: a Critical Review," J Optom, Jan.-Mar. 2009 2(1): 3-18.

Okabe et al., "Intraocular tissue distribution of betamethasone after intrascleral administration using a non-biodegradable sustained drug delivery device," Investigative Ophthalmology and Visual Science. 2003;44:2702-2707. Downloaded from the Internet: <<http://www.iovs.Org/cgi/reprint/44/6/2702>>.

Rosenfeld, "The Latest Research: Intravitreal Bevacizumab for Proliferative Diabetic Retinopathy," Review of Ophthalmology's Retina Online, Feb. 2006; retrieved from the Internet: http://www.revophth.com/archive/newsletter/0206_retina.htm. 2 pages.

Smith et al., "Spectrophotometric determination of pKa values for fluorescein using activity coefficient corrections," WaterSA 2002; 28(4):395-402.

Soheilian et al., "Pilot Study of Intravitreal Injection of Diclofenac for Treatment of Macular Edema of Various Etiologies," Retina, Mar. 2010; 30(3): 509-515.

Theodossiadis et al., "Intravitreal administration of the anti-tumor necrosis factor agent infliximab for neovascular age-related macular degeneration," Am J Ophthalmol. May 2009;147(5):825-830.

Williams et al., "Treating Diabetic Macular Edema With Ocular NSAIDs," Retinal Physician, Nov. 2007; retrieved from the Internet Nov. 11, 2007. http://www.retinalphysician.com/article.aspx?article=101096>, 5 pages total.

* cited by examiner

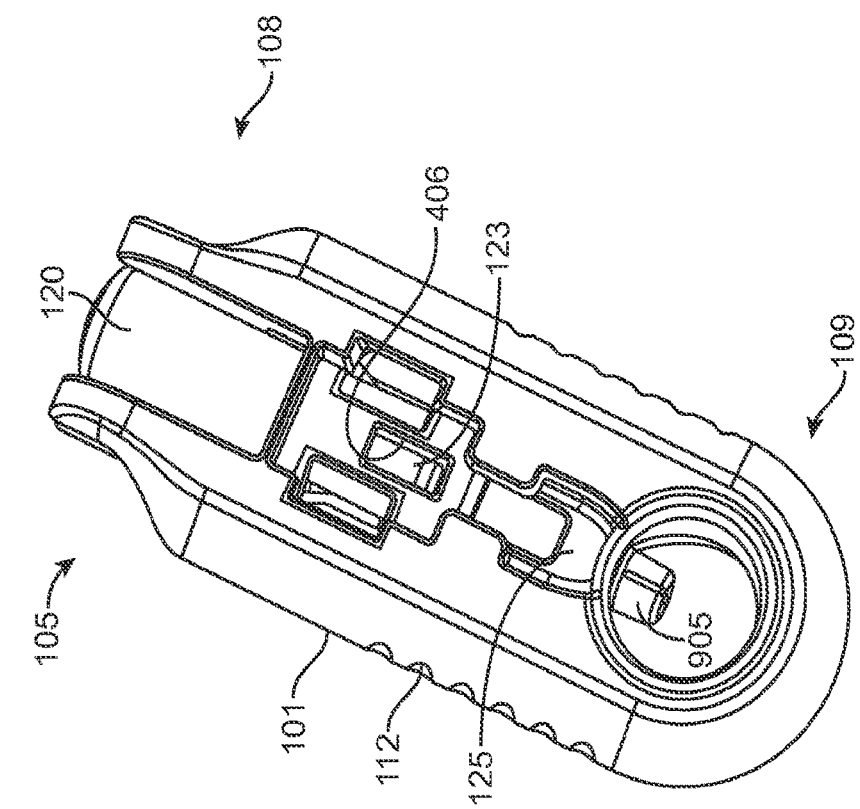
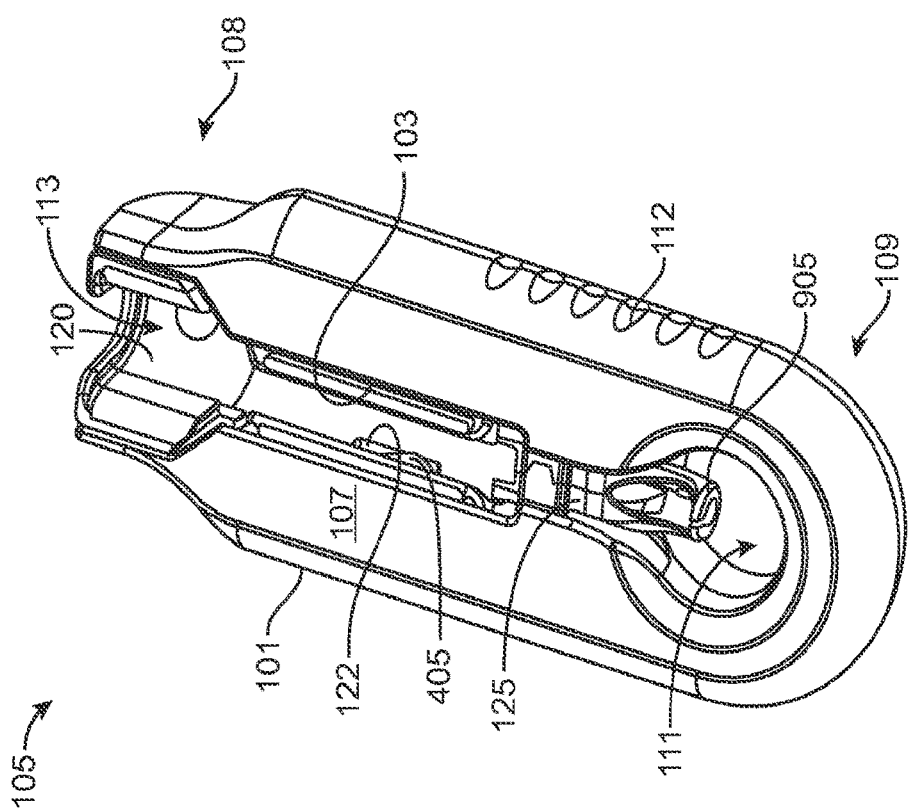
FIG. 2B
FIG. 2A

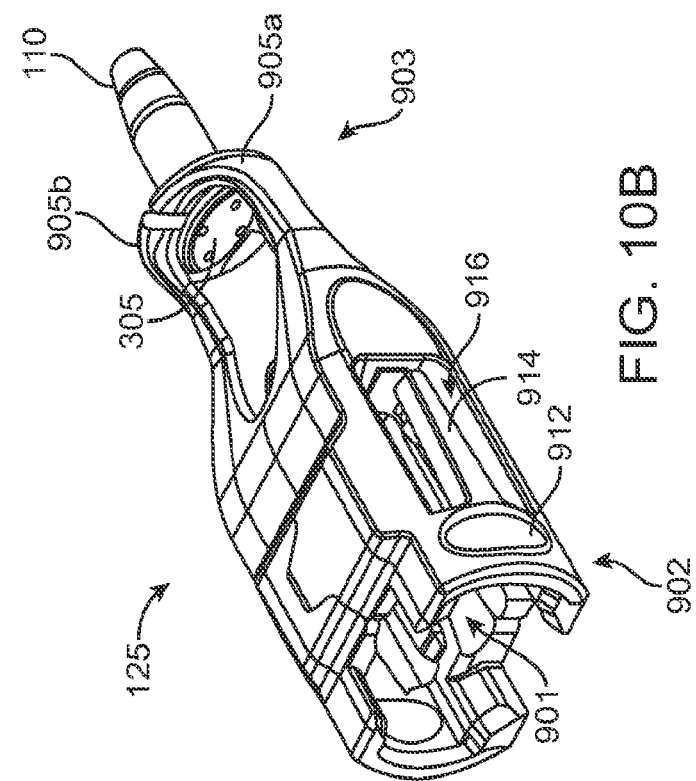
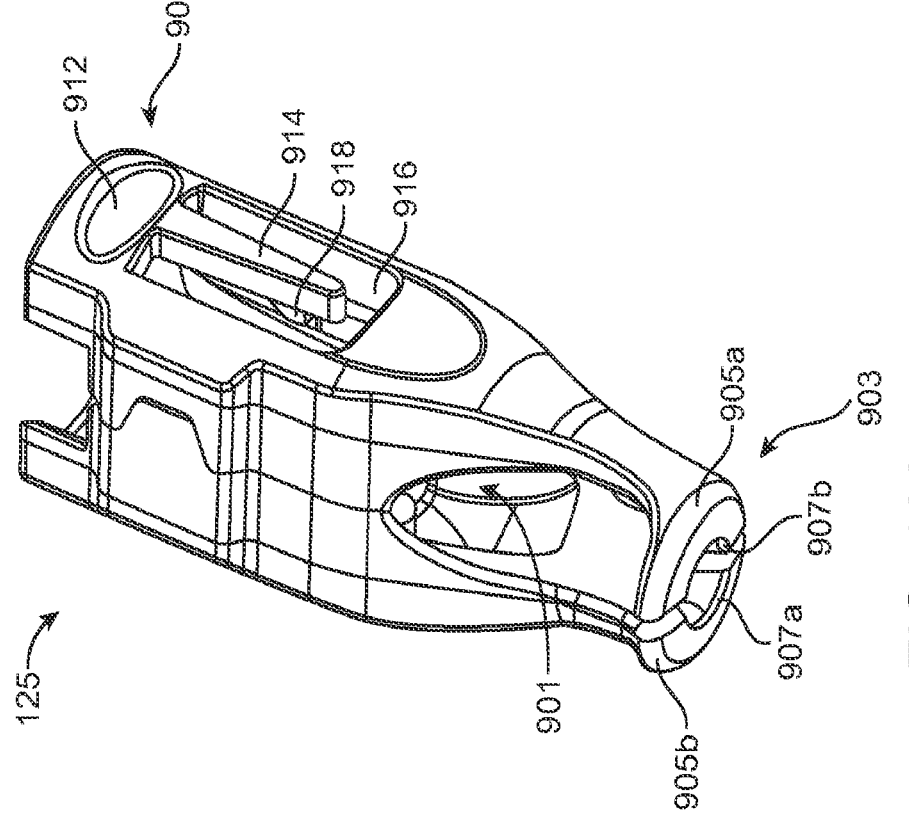
FIG. 10A
FIG. 10B

OCULAR IMPLANT DELIVERY DEVICE AND METHOD

CROSS-REFERENCE TO PRIORITY DOCUMENTS

This application claims priority under 35 U.S.C. § 119(e) of U.S. Provisional Patent Application Ser. No. 62/024,682, filed Jul. 15, 2014. The disclosure of the provisional patent application is hereby incorporated by reference in its entirety.

FIELD

The subject matter described herein relates to methods, systems and devices for holding, filling and/or delivering implantable drug delivery devices.

BACKGROUND

Implantable devices can be used to provide a therapeutic agent to one or more locations of a patient. The implant may have a reservoir for holding therapeutic agent, and a structure to retain the implant at a desired location of the patient. The agent can be released from the implant into the patient to provide a therapeutic benefit. After an amount of time, the amount of fluid released can be less than ideal, and the fluid of the implant may be replaced, refilled, or exchanged to provide additional amounts of therapeutic agent to extend the therapy. A drug delivery device may be implanted into a patient's eye for the delivery of drug to the eye in treating eye disease. U.S. Pat. No. 8,399,006, which is incorporated herein by reference, describes an example of an implantable drug delivery device for the eye.

There remains a need for devices and methods for filling implants with drug and for holding the implantable device during insertion of the device into the patient.

SUMMARY

Implementations of the present disclosure provide methods, systems and devices for filling implants with drug and for holding the implantable device during insertion of the device into the patient. In many implementations, the methods, systems and devices provide for injection of a therapeutic agent into an implantable device prior to insertion. The implantable device can be manufactured and provided to a clinic without a therapeutic agent, such that the therapeutic agent can be placed in the implantable device in the clinic prior to insertion.

In one aspect, provided is an ocular implant system having an ocular implant having a retention structure and a reservoir sized and shaped to be inserted at least partially into an eye such that the implant can deliver a drug from the reservoir into the eye. The system has a carrier member with a shell having a central channel extending at least partially through the shell from a proximal end towards a distal end of the shell; and a guide sleeve removably attached within at least a first region of the central channel of the shell, the guide sleeve defining a proximal port into the central channel that is accessible from the proximal end of the shell. The system includes an implant holder removably attached within at least a second region of the central channel of the shell adjacent to a distal end of the guide sleeve. The implant holder has a pair of graspers adapted to releasably secure the implant at a distal end of the implant holder.

The system can further include a fill syringe sized and shaped to be inserted through the port into the central channel through the guide sleeve to fill the implant with one or more therapeutic agents. The guide sleeve can simultaneously detach from the shell and attach to the fill syringe when the fill syringe is inserted into the central channel. The guide sleeve can have at least one guide sleeve slot sized and shaped to receive a corresponding tab of the shell that projects into the at least one guide sleeve slot when the guide sleeve is positioned within the central channel. An edge of the guide sleeve slot can abut a distal end of the shell tab when in a locked first state. The fill syringe can have a needle assembly having an outer surface, and optionally the fill syringe can be pre-filled with the one or more therapeutic agents. Insertion of the fill syringe through the guide sleeve positioned within the central channel can cause contact between the outer surface of the needle assembly and an inner surface of the shell tab urging the shell tab to flex outward away from the guide sleeve slot into an unlocked second state wherein the edge of the guide sleeve slot no longer abuts the distal end of the shell tab.

A region of the guide sleeve can have a u-shaped slot forming a guide sleeve tab. The guide sleeve tab can have a free end that projects inwards towards a longitudinal axis of the guide sleeve positioned within the central channel. The fill syringe can have a first portion having a first outer diameter and a second portion having a second outer diameter. The first portion can be located distal to the second portion and the first outer diameter can be larger than the second outer diameter. Distal advancement of the fill syringe through the guide sleeve can cause the first portion of the fill syringe to abut against the free end of the guide sleeve tab and can urge the guide sleeve tab outward away from the longitudinal axis of the guide sleeve. Further distal advancement of the fill syringe through the guide sleeve can advance the first portion distal to the free end of the guide sleeve tab such that the free end flexes back inward toward the longitudinal axis and towards the smaller diameter second portion located proximal to the first portion. The free end of the guide sleeve tab can abut a proximal ledge of the first portion locking the guide sleeve to the fill syringe. The implant holder can have an interior configured to receive at least a portion of the needle assembly of the fill syringe.

The pair of graspers can extend substantially around the retention structure of the implant such that a fill port of the implant is available from within the interior of the implant holder. A first grasper of the pair of graspers can have a first protrusion and a second grasper of the pair of graspers can have a second protrusion. The first and second protrusions can be configured to be received within an indentation distal to the retention structure of the implant such that the retention structure is held within the interior of the implant holder and the reservoir extends distal to the implant holder.

The system can further include a handle member usable for inserting the implant into an eye. The implant holder can be configured to interchangeably couple with the carrier member and the handle member. The handle member can include an elongated proximal portion and a distal attachment portion. The distal attachment portion can releasably attach to the implant holder. The distal attachment portion of the handle member can be sized and shaped to be inserted through the central channel after the fill syringe and guide sleeve coupled to the fill syringe are removed from the shell. The distal attachment portion can include a first arm and a second arm. A proximal end region of the implant holder can have a pair of tabs formed by a pair of u-shaped slots. Each of the pair of tabs can have a projection on its inner surface.

The first arm and the second arm can each have a recess on its outer surface. Each of the recesses can be configured to receive the projections when the first and second arms are inserted through the interior of the implant holder.

The handle member can further include an actuator configured to detach the implant from the implant holder. When the actuator is in a first state, the pair of graspers can be positioned adjacent one another and surround the implant. When the actuator is in a second state, the pair of graspers can be urged away from one another and release the implant. The actuator can include an actuator element, a spring-held slider member, and a pair of arms. The actuator element can have a projection extending from a lower surface and have a ramped surface. Movement of the actuator element towards the upper surface of the handle can cause the ramped surface to slide against a corresponding ramped surface of the slider member urging the slider member in a proximal direction relative to the pair of arms. The slider member can have a forked region interfaced with the pair of arms such that proximal movement of the slider member causes the pair of arms to open in a scissor-like movement. Opening the pair of arms can urge the pair of graspers away from one another releasing the implant held therebetween.

The central channel can terminate at a window extending through a distal end region of the shell. The pair of graspers can secure the implant within the window. The implant can have an elongate axis extending through a center of the implant from a proximal end to the distal end of the implant. The elongate axis of the implant can be concentric with an elongate axis of the central channel. A proximal end of the guide sleeve can be relatively flush with the proximal end of the shell. A proximal end of the guide sleeve can extend a distance beyond the proximal end of the shell. The proximal end of the guide sleeve can incorporate a gripping element. The gripping element can have an ergonomic size and shape that facilitates grasping by a user. The guide sleeve can have a generally cylindrical shape. The guide sleeve can have a c-shaped cross section such that a first side of the guide sleeve is cylindrical and a second side of the guide sleeve is discontinuous. The discontinuous second side of the guide sleeve can align with the first side of the shell and the central channel.

In an interrelated aspect, provided is an ocular implant handling system having a carrier member. The carrier member has a shell having a central channel extending at least partially through the shell from a proximal end towards a distal end of the shell. The carrier member has a guide sleeve removably attached within at least a first region of the central channel of the shell. The guide sleeve defines a proximal port into the central channel that is accessible from the proximal end of the shell. The carrier member has an implant holder removably attached within at least a second region of the central channel of the shell adjacent to a distal end of the guide sleeve. The implant holder has a pair of graspers adapted to releasably secure an implant at a distal end of the implant holder.

The handle member can be usable for inserting an implant into an eye. The system can further include an ocular implant having a retention structure and a reservoir sized and shaped to be inserted at least partially into an eye such that the implant can deliver a drug from the reservoir into the eye.

The system can further include a fill syringe sized and shaped to be inserted through the port into the central channel through the guide sleeve. The guide sleeve can simultaneously detach from the shell and attach to the fill syringe when the fill syringe is inserted into the central channel. The guide sleeve can have at least one guide sleeve slot sized and shaped to receive a corresponding tab of the shell that projects into the at least one guide sleeve slot when the guide sleeve is positioned within the central channel. An edge of the guide sleeve slot can abut a distal end of the shell tab when in a locked first state. The fill syringe can have a needle assembly having an outer surface. Insertion of the fill syringe through the guide sleeve positioned within the central channel can cause contact between the outer surface of the needle assembly and an inner surface of the shell tab urging the shell tab to flex outward away from the guide sleeve slot into an unlocked second state wherein the edge of the guide sleeve slot no longer abuts the distal end of the shell tab. A region of the guide sleeve can have a u-shaped slot forming a guide sleeve tab. The guide sleeve tab can have a free end that projects inwards towards a longitudinal axis of the guide sleeve positioned within the central channel.

The fill syringe can have a first portion having a first outer diameter and a second portion having a second outer diameter. The first portion can be located distal to the second portion and the first outer diameter can be larger than the second outer diameter. Distal advancement of the fill syringe through the guide sleeve can cause the first portion of the fill syringe to abut against the free end of the guide sleeve tab and urge the guide sleeve tab outward away from the longitudinal axis of the guide sleeve. Further distal advancement of the fill syringe through the guide sleeve can advance the first portion distal to the free end of the guide sleeve tab such that the free end flexes back inward toward the longitudinal axis and towards the smaller diameter second portion located proximal to the first portion. The free end of the guide sleeve tab can abut a proximal ledge of the first portion locking the guide sleeve to the fill syringe.

The implant holder can have an interior configured to receive at least a portion of the needle assembly of the fill syringe. The pair of graspers can extend substantially around the retention structure of the implant such that a fill port of the implant is available from within the interior of the implant holder. A first grasper of the pair of graspers can have a first protrusion and a second grasper of the pair of graspers can have a second protrusion. The first and second protrusions can be configured to be received within an indentation distal to the retention structure of the implant such that the retention structure is held within the interior of the implant holder and the reservoir extends distal to the implant holder.

The handle member can include an elongated proximal portion and a distal attachment portion. The distal attachment portion can releasably attach to the implant holder. The distal attachment portion of the handle member can be sized and shaped to be inserted through the central channel after the fill syringe and guide sleeve coupled to the fill syringe are removed from the shell. The distal attachment portion can include a first arm and a second arm. A proximal end region of the implant holder can have a pair of tabs formed by a pair of u-shaped slots. Each of the pair of tabs can have a projection on its inner surface. The first arm and the second arm can each have a recess on its outer surface. Each of the recesses can be configured to receive the projections when the first and second arms are inserted through the interior of the implant holder.

The handle member can further include an actuator configured to detach the implant from the implant holder. When the actuator is in a first state, the pair of graspers can be positioned adjacent one another and surround the implant. When the actuator is in a second state, the pair of graspers can be urged away from one another and release the implant.

The actuator can include an actuator element, a spring-held slider member, and a pair of arms. The actuator element can have a projection extending from a lower surface and having a ramped surface. Movement of the actuator element towards the upper surface of the handle can cause the ramped surface to slide against a corresponding ramped surface of the slider member urging the slider member in a proximal direction relative to the pair of arms. The slider member can have a forked region interfaced with the pair of arms such that proximal movement of the slider member causes the pair of arms to open in a scissor-like movement. Opening the pair of arms can urge the pair of graspers away from one another releasing an implant held therebetween.

The central channel can terminate at a window extending through a distal end region of the shell. The pair of graspers can secure an implant within the window. An implant can have an elongate axis extending through a center of the implant from a proximal end to the distal end of the implant. The elongate axis of the implant can be concentric with an elongate axis of the central channel. A proximal end of the guide sleeve can be relatively flush with the proximal end of the shell. A proximal end of the guide sleeve can extend a distance beyond the proximal end of the shell. The proximal end of the guide sleeve can incorporate a gripping element. The gripping element can have an ergonomic size and shape that facilitates grasping by a user. The guide sleeve can have a generally cylindrical shape. The guide sleeve can have a c-shaped cross section such that a first side of the guide sleeve is cylindrical and a second side of the guide sleeve is discontinuous. The discontinuous second side of the guide sleeve can align with the first side of the shell and the central channel.

In an interrelated aspect, provided is an ocular implant handling and delivery system. The system includes a handle member usable for inserting an ocular implant into an eye having an elongated proximal portion and a distal attachment portion. The system includes a carrier member having a shell having a central channel extending at least partially through the shell from a proximal end towards a distal end of the shell; and a guide sleeve removably attached within at least a first region of the central channel of the shell. The guide sleeve defines a proximal port into the central channel that is accessible from the proximal end of the shell. The system includes an implant holder removably attached within at least a second region of the central channel of the shell adjacent to a distal end of the guide sleeve. The implant holder has a pair of graspers adapted to releasably secure the ocular implant at a distal end of the implant holder. The implant holder is configured to interchangeably couple with the carrier member and the handle member.

The system can further include the ocular implant. The ocular implant can include a retention structure and a reservoir sized and can be shaped to be inserted at least partially into an eye such that the ocular implant can deliver a drug from the reservoir into the eye.

In an interrelated aspect, provided is an ocular implant handling and filling system. The system includes a carrier member having a shell having a central channel extending at least partially through the shell from a proximal end towards a distal end of the shell; and a guide sleeve removably attached within at least a first region of the central channel of the shell. The guide sleeve defines a proximal port into the central channel that is accessible from the proximal end of the shell. The system includes an implant holder removably attached within at least a second region of the central channel of the shell adjacent to a distal end of the guide sleeve. The implant holder has a pair of graspers adapted to releasably secure an ocular implant at a distal end of the implant holder. The system includes a fill syringe sized and shaped to be inserted through the port into the central channel through the guide sleeve.

The system can further includes the ocular implant having a retention structure and a reservoir sized and shaped to be inserted at least partially into an eye such that the implant can deliver a drug from the reservoir into the eye. The system can further include a handle member usable for inserting an ocular implant into an eye. The handle member can include an elongated proximal portion and a distal attachment portion. The implant holder can be configured to interchangeably couple with the carrier member and the handle member.

In an interrelated aspect, provided is a handling and filling system having a carrier member. The carrier member includes a shell having a central channel extending at least partially through the shell from a proximal end towards a distal end of the shell. The carrier member includes a guide sleeve removably attached within at least a first region of the central channel of the shell. The guide sleeve defines a proximal port into the central channel that is accessible from the proximal end of the shell. The system includes an implant holder removably attached within at least a second region of the central channel of the shell adjacent to a distal end of the guide sleeve. The implant holder has a pair of graspers adapted to releasably secure an implant at a distal end of the implant holder. The system includes a fill syringe sized and shaped to be inserted through the port into the central channel through the guide sleeve. The system includes a handle member usable for inserting the implant into an eye. The handle member includes an elongated proximal portion and a distal attachment portion. The implant holder is configured to interchangeably couple with the carrier member and the handle member.

The system can further include the ocular implant. The ocular implant can include a retention structure and a reservoir sized and shaped to be inserted at least partially into an eye such that the ocular implant can deliver a drug from the reservoir into the eye.

In an interrelated aspect, provided is a fill syringe sized and shaped to insert through a region of a carrier member holding an ocular implant. The fill syringe is configured to inject one or more therapeutic agents from the fill syringe into a reservoir of the ocular implant.

The carrier member can include a shell having a central channel extending at least partially through the shell from a proximal end towards a distal end of the shell. The carrier member can include a guide sleeve removably attached within at least a first region of the central channel of the shell. The guide sleeve can define a proximal port into the central channel that is accessible from the proximal end of the shell. A portion of the fill syringe can lock with a portion of the guide sleeve when the fill syringe is inserted through the central channel of the shell. Withdrawal of the fill syringe from the carrier member can remove the guide sleeve from the shell. The fill syringe can be pre-filled with the one or more therapeutic agents.

The above-noted aspects and features may be implemented in systems, apparatus, and/or methods, depending on the desired configuration. The details of one or more variations of the subject matter described herein are set forth in the accompanying drawings and the description below. Features and advantages of the subject matter described herein will be apparent from the description and drawings, and from the claims.

BRIEF DESCRIPTION OF THE DRAWINGS

In the drawings,

FIGS. 2A and 2B show front and back sides, respectively, of a carrier of the system of FIG. 1A;

FIG. 10A shows an implementation of an implant holder for use with the system;

FIG. 10B shows the implant holder of FIG. 10A holding an implant;

DETAILED DESCRIPTION

Described herein are methods, devices and systems for easily, reproducibly, and safely filling an ocular implant with a material, such as a drug, and inserting the implant into a patient, such as a patient's eye. Although specific reference is made to placement of devices in the eye, systems described herein can be used with many devices used in locations other than the eye, such as in orthopedic, dental, intraluminal and transdermal locations. The systems and methods described herein are well suited for use with many drug delivery devices, such as refillable diffusion based devices, and can be exceptionally well suited for diffusion devices having a porous drug release structure configured for extended release in which the porous structure inhibits flow of fluid during exchange.

Figure 1A:
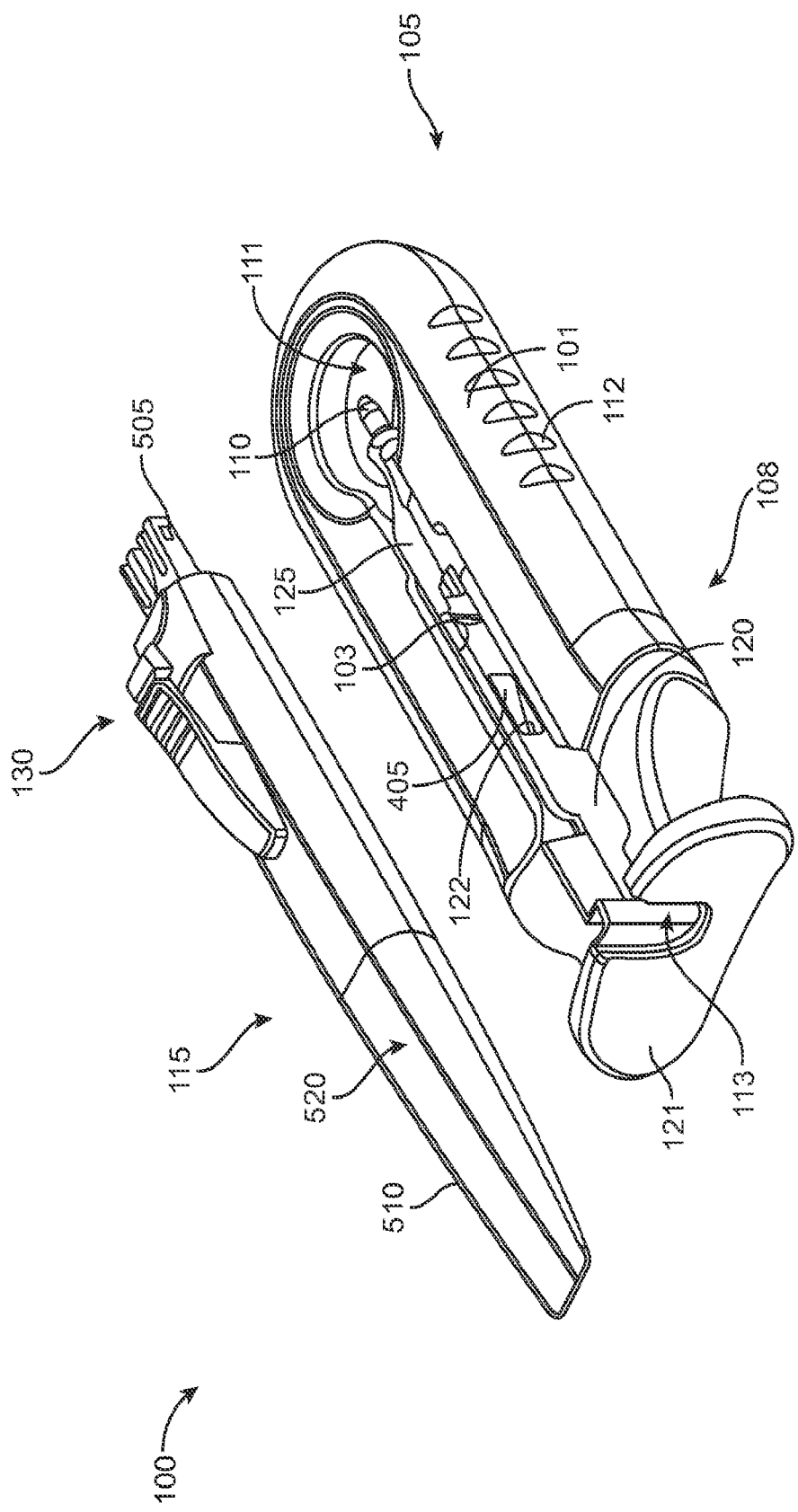
FIG. 1A shows an implementation of a system for holding an ocular implant, filling the ocular implant with a drug and inserting the filled implant into an eye.

FIG. 1A shows an implementation of a system for holding, filling, and/or delivering an ocular implant. The system 100 can include an ocular implant handling system including an implant carrier member 105 and a handle member 115. The system 100 can further include a fill syringe 205 (see FIG. 1B). The fill syringe 205 can contain a therapeutic agent, such as a pre-filled syringe. The carrier member 105 is sized and shaped to initially store an implant 110 prior to implantation of the implant 110 into the eye. The fill syringe 205 can interface with the carrier member 105 to fill the implant 110 with a flowable material, such as a liquid drug or therapeutic agent. The fill syringe 205 can interdigitate with the carrier member 105 holding the implant 110 and lock into a portion of the carrier member 105 (e.g. a guide sleeve), as will be described in more detail below. The therapeutic agent or agents suitable for use with the implant 110 can vary, for example, as described in U.S. Pat. No. 8,623,395, entitled "Implantable Therapeutic Device," which is incorporated here in its entirety. The therapeutic agent can include one or more of a variety of active ingredients of the therapeutic agent, a formulation of the therapeutic agent, a commercially available formulation of the therapeutic agent, a physician prepared formulation of therapeutic agent, a pharmacist prepared formulation of the therapeutic agent, or a commercially available formulation of therapeutic agent having an excipient. The therapeutic agent may be referred to with generic name or a trade name.

A portion of the carrier member 105 can guide and properly align a cannula or needle 210 of the syringe 205 with the fill port of the implant 110. The syringe 205 can interdigitate with this portion of the carrier member 105 and lock into it such that when the syringe 205 is removed, for example, after filling the implant 110 with the drug from the syringe 205, the syringe 205 and this portion of the carrier member 105 locked onto the syringe can be withdrawn together. As will be described in more detail below, once the fill syringe 205 is removed (e.g. after the implant 110 is filled with drug), the handle member 115 can be inserted into the carrier member 105 and used to remove the implant 110 from the carrier member 105. The handle member 115 and the carrier member 105 can interchangeably couple to the implant 110. The handle member 115 can be coupled to the carrier member 105 in a manner that attaches the implant 110 to the handle member 115 and detaches the implant 110 from the carrier member 105. The handle member 115 can then be used to position the implant 110 and insert the implant 110 into an eye. Each of these features will be described in more detail below. It should be appreciated that the implant 110 can be pre-filled and stored within the carrier member 105. Alternatively, the implant 110 can be stored within the carrier member 105 while empty and filled prior to implantation in the eye, such as using a pre-filled syringe. It should also be appreciated that the implant 110 can be filled after implantation in the eye.

Generally, the implant 110 to be used with the system 100 described herein can include an internal reservoir. The reservoir can be a rigid-walled reservoir having a fixed volume. Alternatively, one or more of the reservoir walls can be configured to expand such that the reservoir volume changes depending on a fill status of the implant 110. The implant 110 can include a proximal retention structure 305 and an indentation 307 or narrowed region that is sized smaller than the retention structure 305. The indentation 307 can also be sized smaller than a shoulder region extending distal to the indentation 307. The indentation 307 can be sized to fit in an elongate incision. The proximal retention structure 305 can include an access port having a penetrable region. For example, the proximal retention structure 305 can include or be covered by a penetrable barrier or septum structure such that the reservoir can be filled with a material. One or more outlets can be positioned in fluid communication with the reservoir of the implant 110 such that therapeutic agent in the reservoir can be delivered to the patient. The one or more outlets can incorporate a porous structure including one or more of many porous structures such as sintered material, openings in a non-permeable material, openings having a size and number to release therapeutic agent at an intended rate, a plurality of holes etched in a material, a semi-permeable membrane, or nano-channels, for example. It should be appreciated that the configuration of implant 110 that can used with the system 100 described herein can vary. The systems described herein can be used with or incorporate features of devices described in U.S. Pat. No. 8,399,006, entitled "Posterior Segment Drug Delivery"; U.S. Pat. No. 8,905,963, entitled "Injector Apparatus and Method for Drug Delivery;" and U.S. Publication No. 2015/0080846, entitled "Insertion and Removal Methods and Apparatus for Therapeutic Devices," the entire disclosures of which are incorporated herein by reference.

As best shown in FIGS. 2A-2B and also FIGS. 3A-3B, 4A-4B, and 5A-5C, the carrier member 105 can include a shell 101 and a guide sleeve 120. The guide sleeve 120 can be removably attached to the shell 101. The system 100 can also include an implant holder 125 configured to releaseably hold an ocular implant 110 within the shell 101. The implant holder 125 can be reversibly coupled to the shell 101 of the carrier member 105. As such that implant holder 125 can be an interchangeable element that can be coupled to the carrier member 105, for example prior to filling with a syringe 205, and can be released from the carrier member 105, for example after filling with a syringe 205 and prior to implantation in a patient using a delivery tool. Thus, the implant holder 125 can be interchangeably coupled with the carrier member and the delivery tool.

The shell 101 of the carrier member 105 can include a central channel 103 extending at least partially through an upper surface of a first side, such as its front side 107, from a proximal end 108 of the carrier member 105 towards a distal end region 109 of the carrier member 105 along a longitudinal axis. The central channel 103 can terminate at an opening or window 111 extending through a distal end region 109 of the shell 101. The implant 110 can be positioned by the implant holder 125 within the window 111. The shell 101 of the carrier member 105 can be generally ergonomically shaped such that a user can hold the carrier member 105 in one hand positioned around the underside of the carrier member 105. The central channel 103 can be available and readily visible on the front side 107 of the carrier member 105. The shell 101 of the carrier member 105 can include one or more textured regions 112 or indentations on its external surface to improve a user's grip on the carrier member 105 during use.

It should be appreciated that reference herein to terms such as "upper," "lower," "upwards," "downwards," "front," "back," "proximal," "distal" are used herein for orientation from one point of view of a user operating the systems described herein and are not intended to be limiting.

The implant 110 can have an elongate axis extending through a center of the implant 110 from the proximal-most end to the distal-most end of the implant 110. The system 100 (and/or each of the components of the system) can also have an elongate axis that is concentric with the elongate axis of the implant 110 forming a longitudinal axis A with which each of the components of the system 100 are substantially aligned. When the implant 110 is held by the implant holder 125 within the carrier member 105, the elongate axis of the implant 110 can be aligned substantially with the longitudinal axis A of the system and the syringe 205 can be inserted substantially along the longitudinal axis A such that the needle 211 penetrates an upper surface of the implant 110. It should be appreciated that the syringe 205 can interdigitate within the central channel 103 along the longitudinal axis A or, in other implementations, can be inserted at an angle to the longitudinal axis A.

As mentioned, the carrier member 105 can include the guide sleeve 120 that can be removably attached within at least a region of the slot of the shell 101. The guide sleeve 120 can define a proximal port 113 into the central channel 103 of the shell 101 that allows for access to the slot from a proximal end of the shell 101. The guide sleeve 120 can help to ensure proper alignment between the syringe 205 and the implant 110 such that a needle 211 of the syringe 205 inserts through a septum or fill port of the implant 110. The guide sleeve 120 can provide guiding alignment during insertion of the syringe 205 through the port 113 into the central channel 103 towards the implant 110 mounted within the implant holder 125 of the carrier member 105.

Figure 1B:
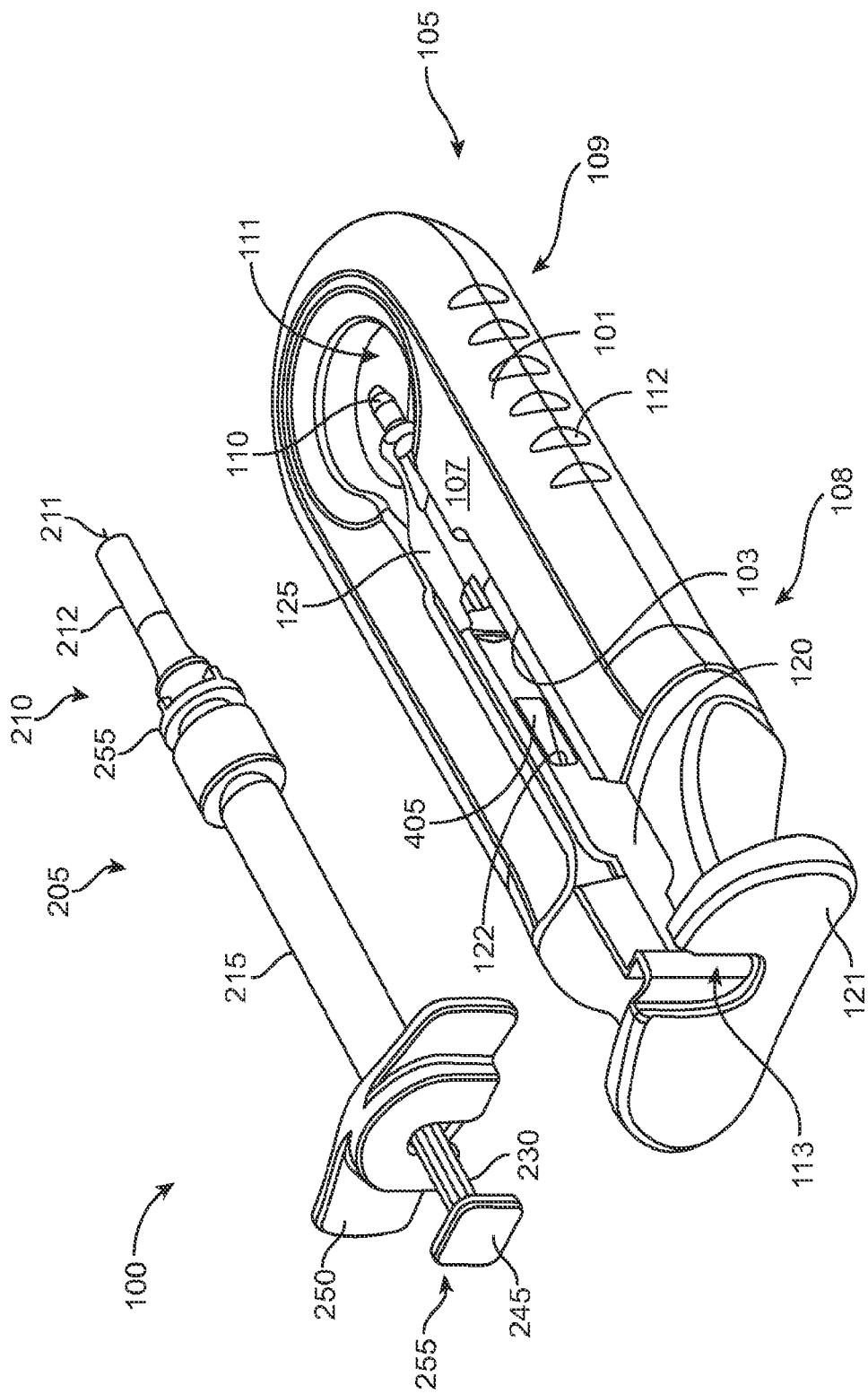
FIG. 1B shows an implementation of a system including a fill syringe.
Figure 3B:
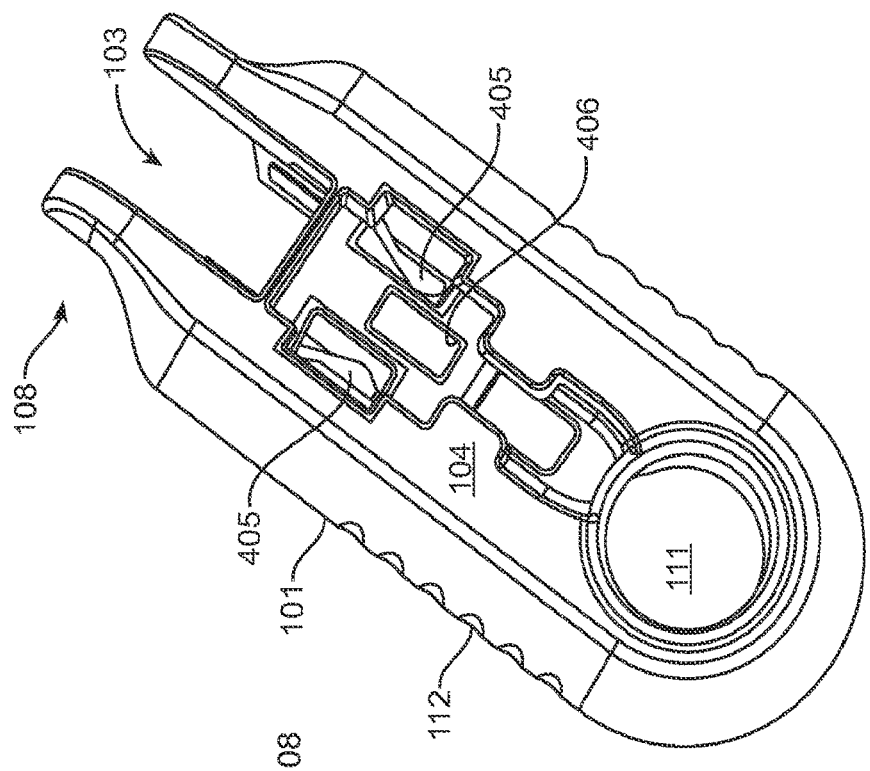
FIGS. 3A and 3B show front and back sides, respectively, of a shell of the system in FIG. 1A.
Figure 3A:
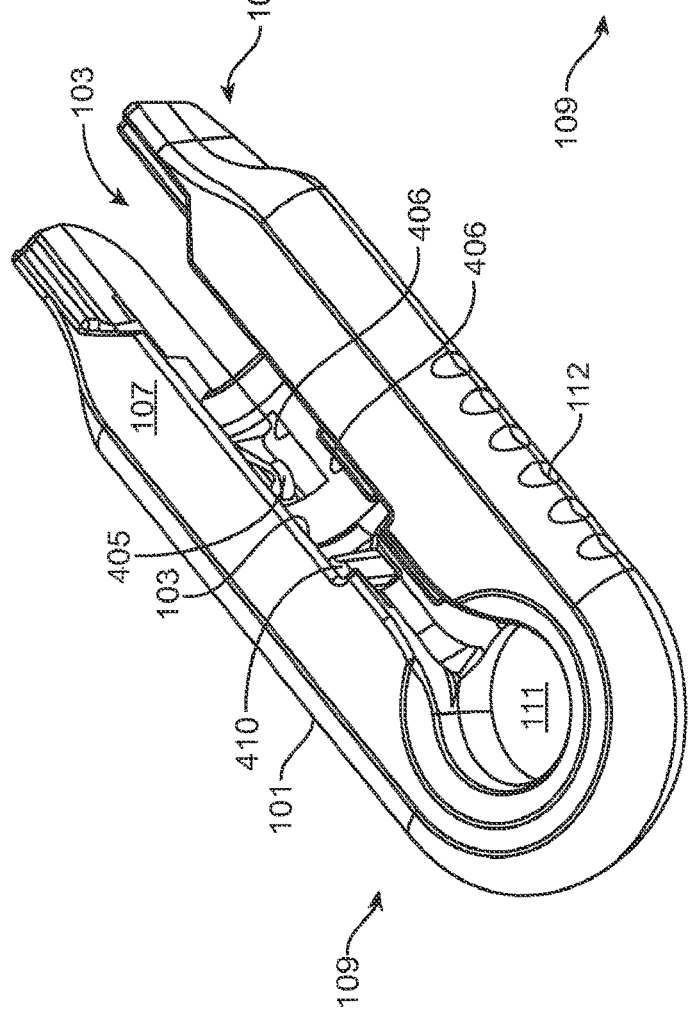
Figure 4B:
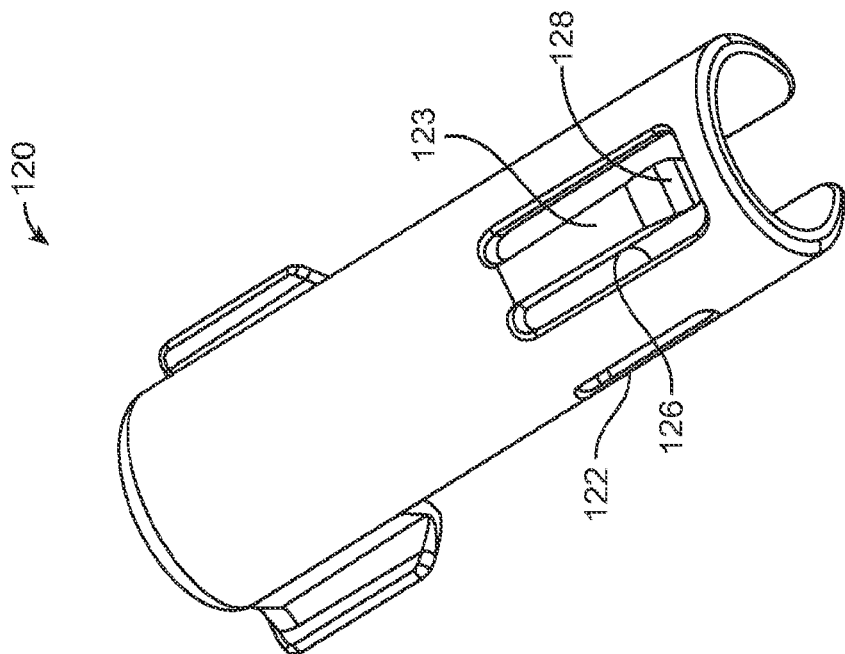
FIGS. 4A and 4B show front and back sides, respectively, of a guide sleeve for use in a system.
Figure 4A:
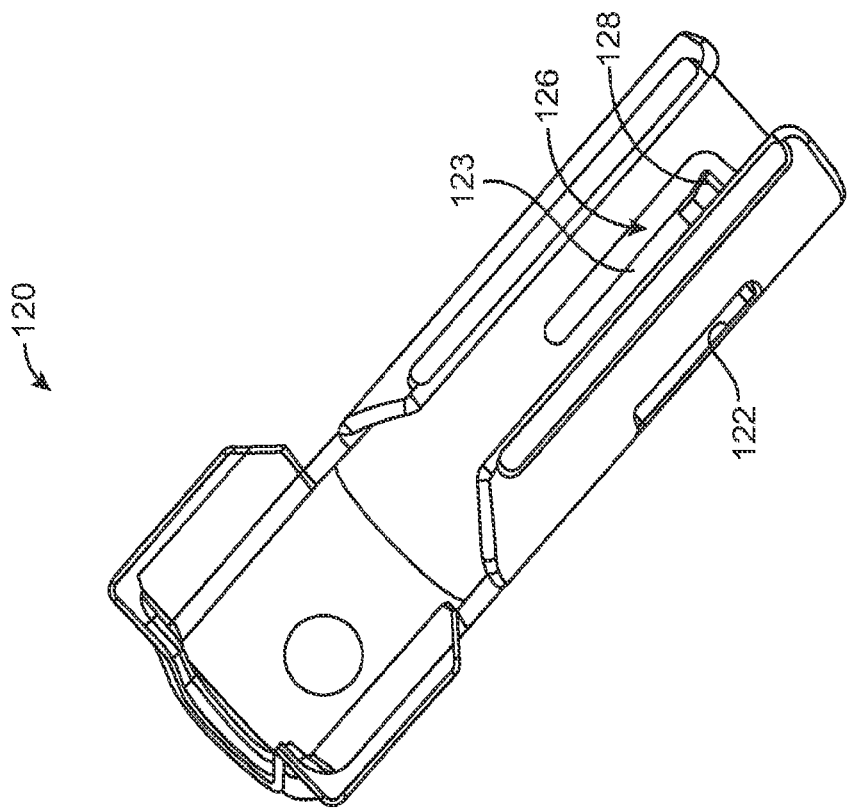
Figure 5B:
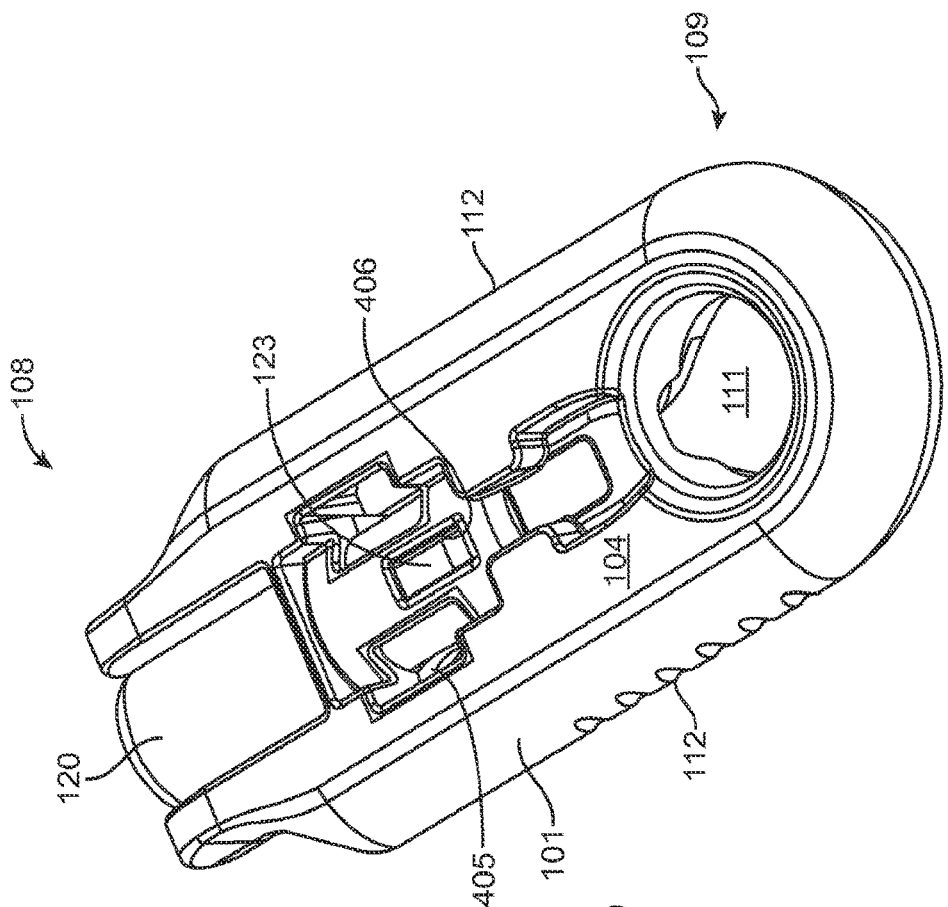
FIGS. 5A, 5B, and 5C show a front, back, and a proximal end view of the guide sleeve coupled to the shell.
Figure 5A:
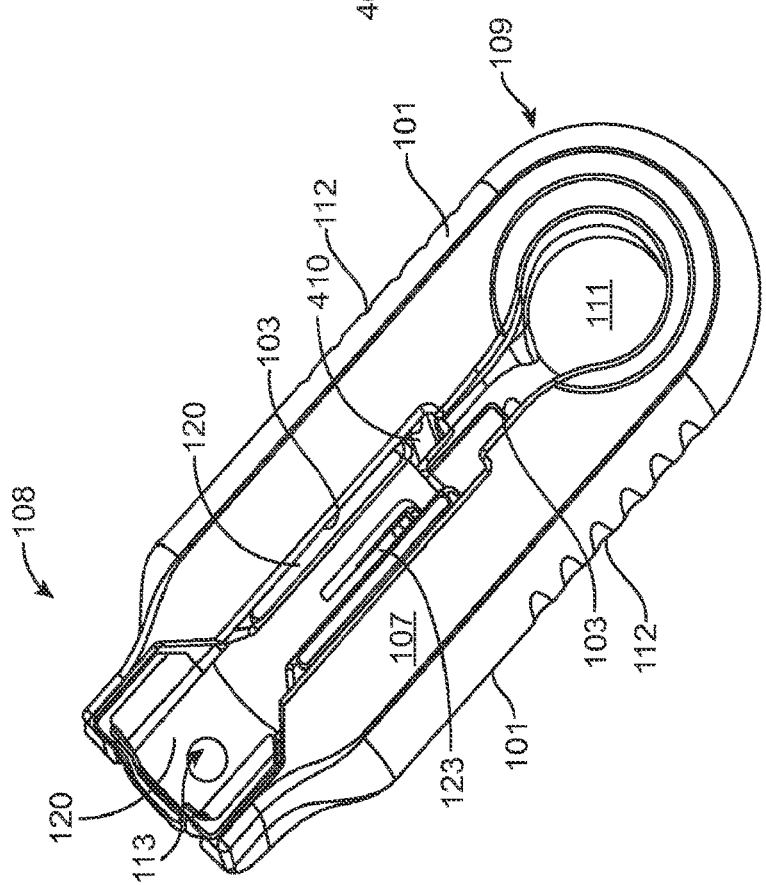
Figure 5C:
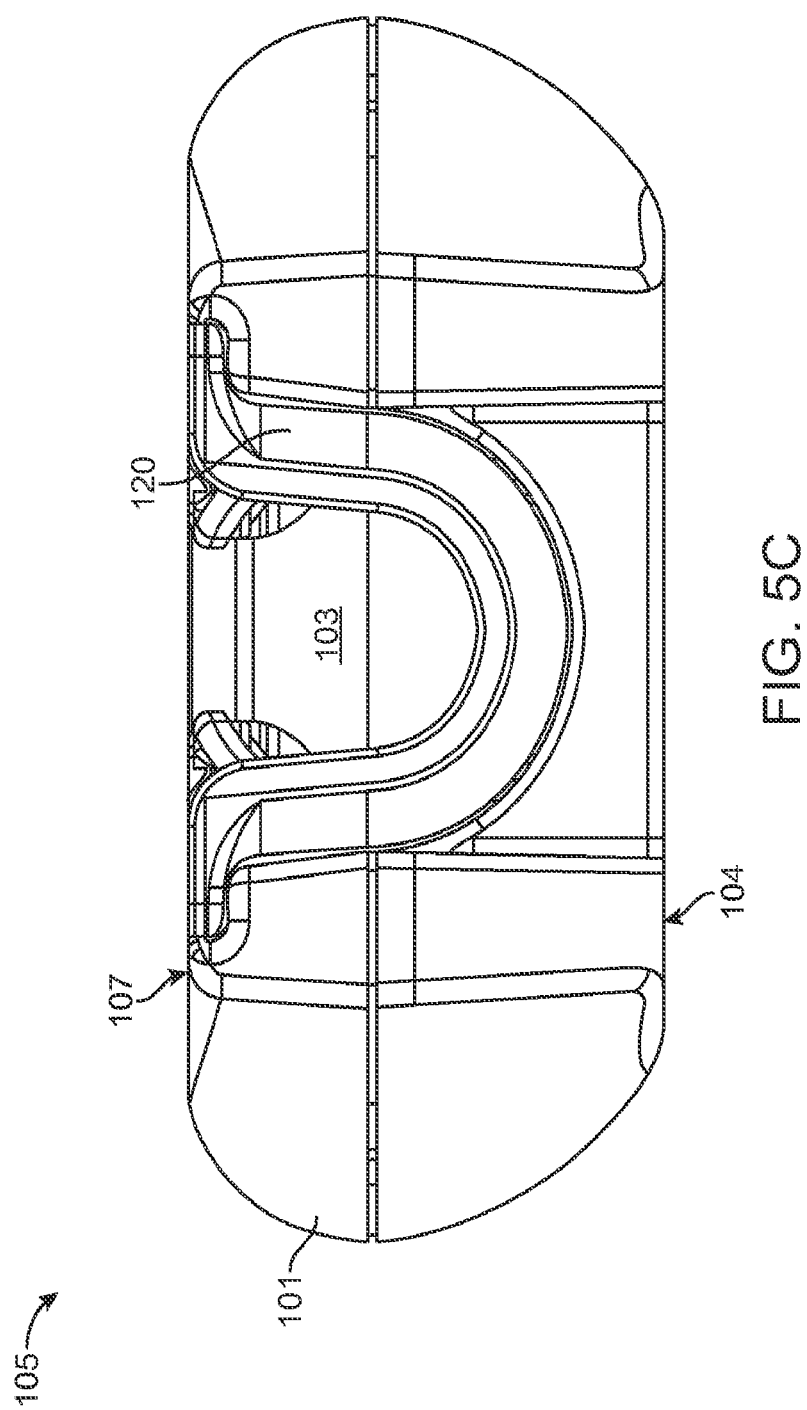

The configuration of the guide sleeve 120 can vary. The guide sleeve 120 can have a length such that it extends a distance between the proximal end 108 of the shell 101 or central channel 103 and a distal region of the central channel 103. The guide sleeve 120 can be relatively flush with a proximal end 108 of the shell 101 (see FIGS. 2A and 2B) or the guide sleeve 120 can extend a distance beyond the proximal end 108 of the shell 101, for example, as shown in FIG. 1A-1B. In this implementation, the guide sleeve 120 can incorporate a gripping element 121. The gripping element 121 of the guide sleeve 120 may have an ergonomic size and shape that facilitates it being grasped by a user, such as between the fingers of a user's hand as will be described in more detail below.

In some implementations, the guide sleeve 120 can have a generally cylindrical shape. The guide sleeve 120 can be a generally cylindrical element having an overall c-shaped cross section such that the underside or back side of the guide sleeve 120 is cylindrical and the front side of the guide sleeve 120 is slotted or discontinuous (see FIGS. 4A-4B and also FIG. 5C). In this implementation when the guide sleeve 120 is reversibly coupled with the shell 101 in the central channel 103, the cylindrical lower surface of the guide sleeve 120 can abut a lower portion 104 of the shell 101 and the discontinuous portion of the guide sleeve 120 can align with the upper surface of the front side 107 of the shell 101.

Figure 9:
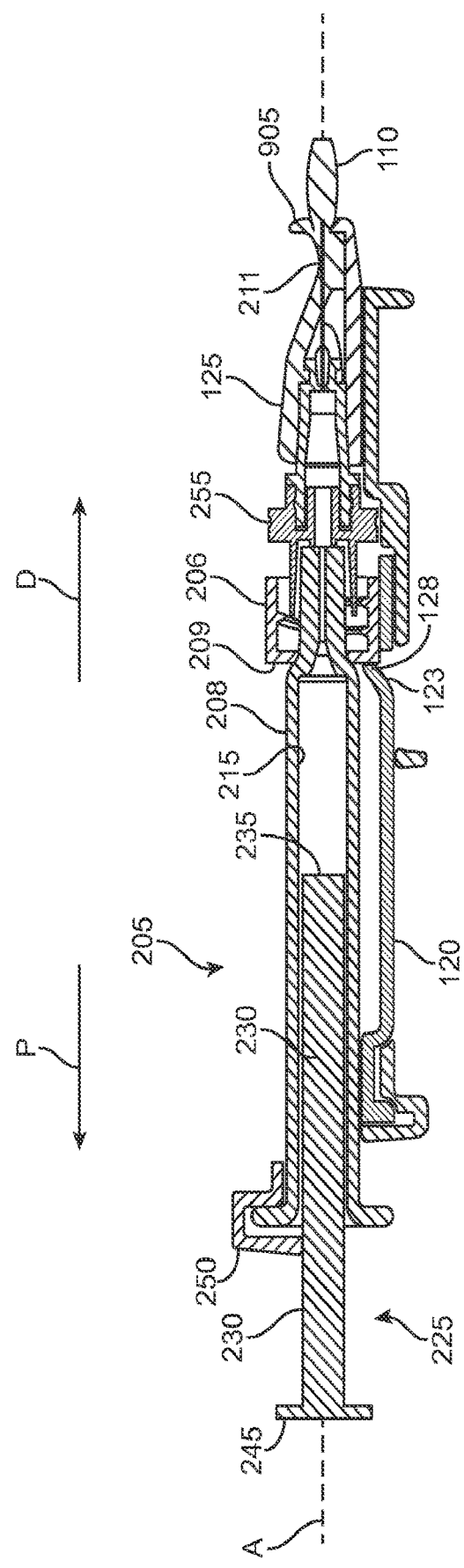
FIG. 9 shows a cross-sectional view of a locking mechanism that locks the guide sleeve to the carrier member.

As mentioned above and as best shown in FIG. 1B and also in FIG. 9, the syringe 205 can have a body sized and shaped to be inserted into the central channel 103 of the shell 101 of the carrier member 105 via the port 113 such that a needle 211 of a needle assembly 210 of the syringe 205 can be inserted into the implant 110 mounted via the implant holder 125 on the carrier member 105. The syringe 205 can fill the implant 110 with a liquid drug or any other liquid prior to inserting the implant 110 into the eye. The syringe 205 can have any of a variety of configurations as known in the art. In some implementations, the syringe 205 can include a reservoir 215 that may be pre-filled with a fluid drug or any other fluid. The reservoir 215 can include a proximal opening configured to receive a mechanism for expelling the fluid from the reservoir 215 through a distal opening of the reservoir 215. The mechanism for expelling the fluid from the reservoir 215 can be a plunger 225 including a piston rod 230 terminating at a piston head 235. The piston head 235 can be configured to contact the liquid to be injected from the reservoir 215 and maintain a seal as the plunger 225 is displaced distally within the reservoir 215. A stop element can be incorporated that prevents withdrawal of the piston rod 230 or piston head 235 through the proximal opening. A proximal end of the syringe 205 can include a flange 245 that can aid in the advancement of the plunger 225 within the reservoir 215 as is known in the art. As the syringe 205 is used to inject material into the implant 110 using the plunger 225, a user can apply a force against an upper surface of the flange 245 (e.g. with the user's thumb) and apply a force against a lower surface of portion 250 (e.g. with a user's finger) therein applying a squeezing pressure to the syringe 205 engaged with the carrier member 105.

The distal opening of the reservoir 215 can be in fluid communication with a needle assembly 210 coupled to the syringe by a luer 255 (see FIG. 1B and FIG. 9). The needle assembly 210 can include a needle 211 and optionally a needle limiter 212 positioned around the needle 211. The needle limiter 212 can have a length such that a distal-most tip of the needle 211 extends only a short distance beyond the needle limiter 212 to prevent penetration of the needle 211 within the implant 110 beyond that short distance so as not to damage the implant 110 during filling. As the distal-most tip of the needle 211 penetrates the septum or fill port of the implant 110, the needle limiter 212 can abut an internal region of the implant holder 125 or an upper surface of the implant 110 preventing the needle 211 from penetrating the implant 110 beyond a desired depth. The syringe 205 can include a needle cap configured to cover the needle 211 and needle limiter 212. The needle assembly 210 may be integrally formed with the syringe 205 or the needle assembly 210 may be detachable from the syringe 205.

Figure 6:
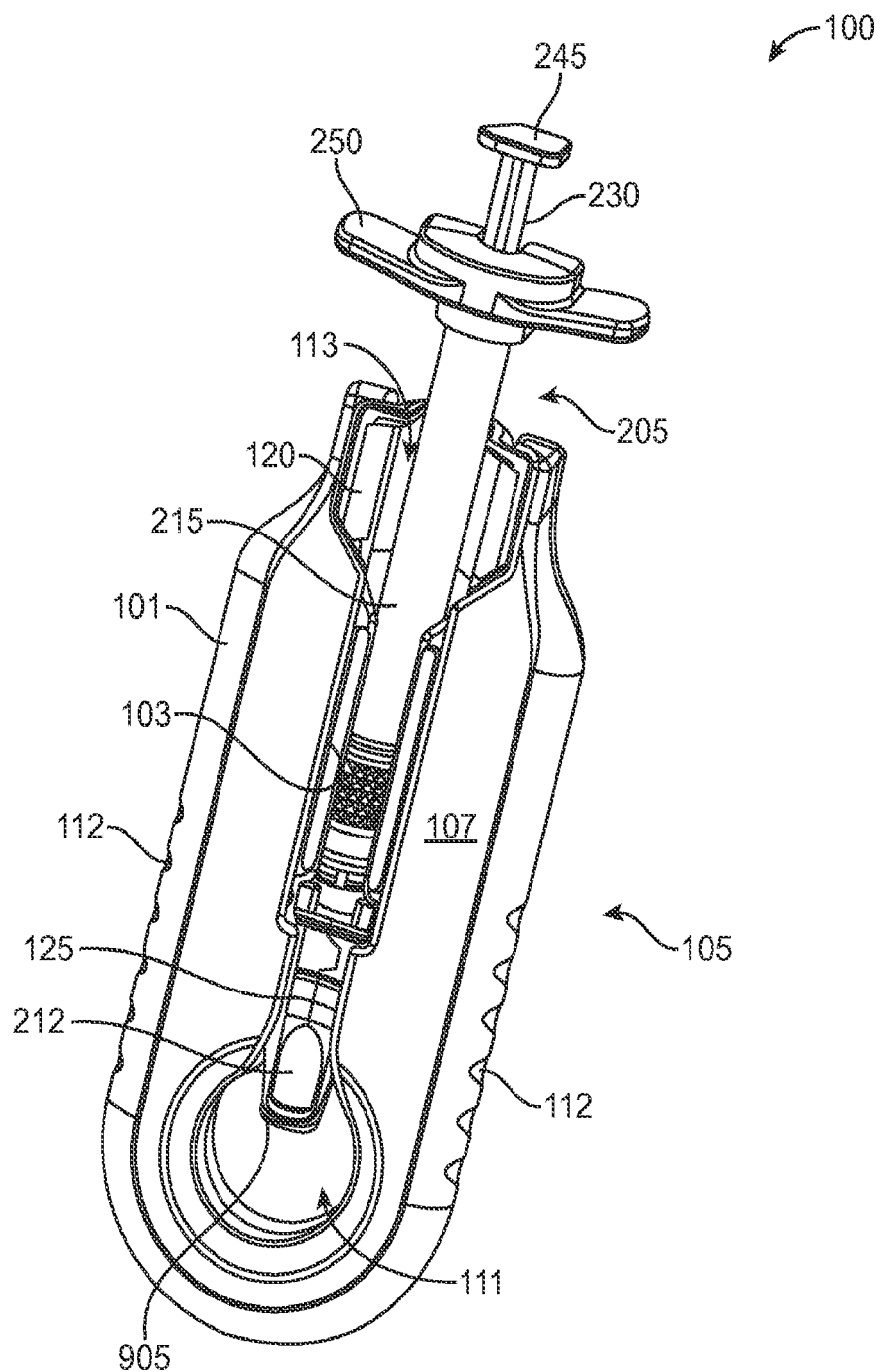
FIG. 6 shows another implementation of a system with the fill syringe coupled to the carrier.
Figure 7:
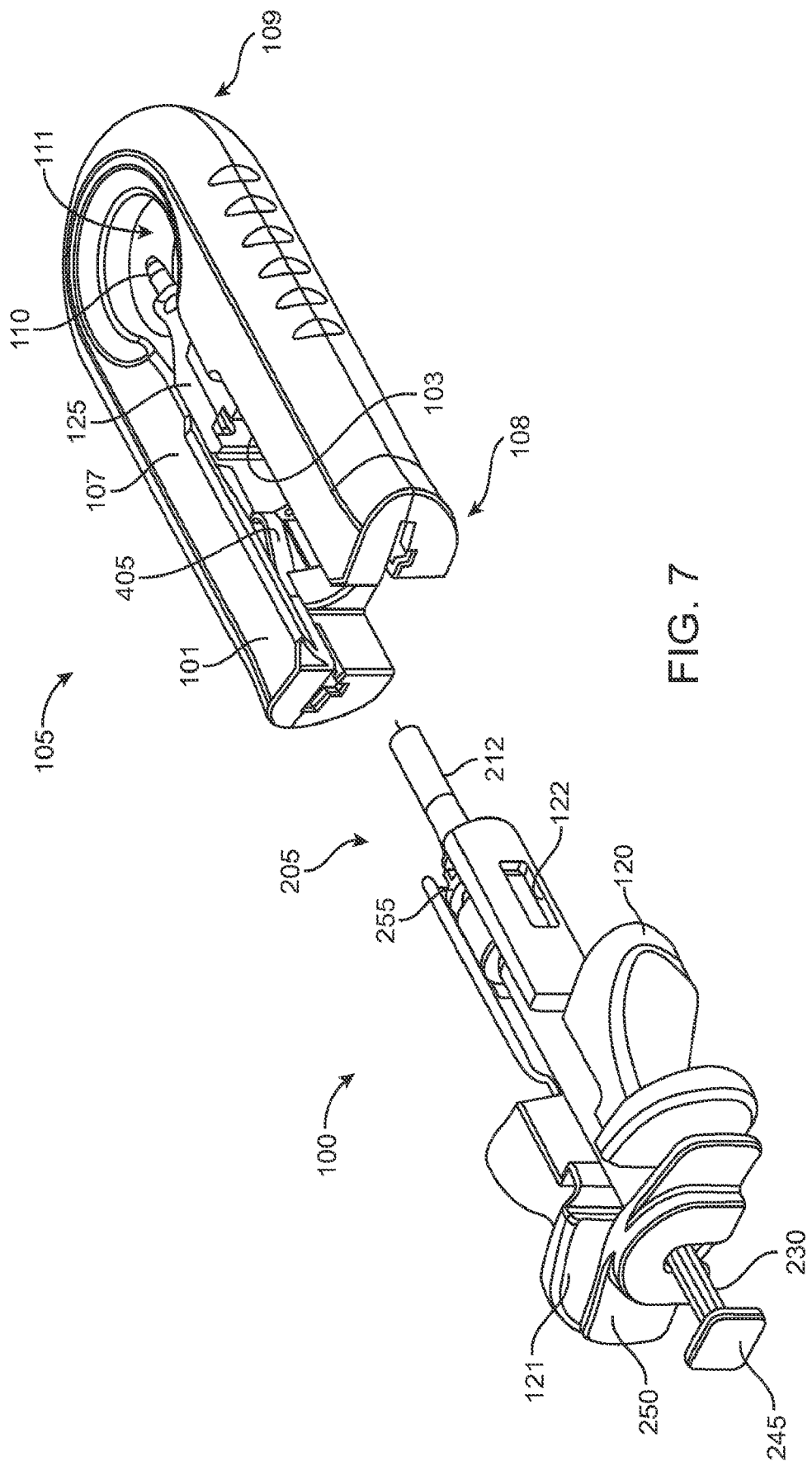
FIG. 7 shows the system of FIG. 1B after the syringe has been used to fill the implant with drug and removed from the carrier.

As mentioned above, the guide sleeve 120 can be removably attached from within the central channel 103 of the shell 101. The shell 101 and/or the guide sleeve 120 can include a locking mechanism that reversibly secures the guide sleeve 120 to the shell 101. The locking mechanism can be released, for example, upon insertion of the syringe 205 as will be described in more detail below. After the syringe 205 has been inserted into the guide sleeve 120 positioned within the central channel 103 of the shell 101 such as to inject drug into the implant 110, the locking mechanism between the guide sleeve 120 and the shell 101 can unlock. The guide sleeve 120 can release from the shell 101 and lock onto the syringe 205 such that both the guide sleeve 120 and the syringe 205 can be removed from the shell 101 upon withdrawal of the syringe 205 from the implant 110. The locking mechanism can simultaneously release the guide sleeve 120 from the shell 101 and lock the guide sleeve 120 onto a region of the syringe 205. When the syringe 205 is inserted into the guide sleeve 120, which can be in locked engagement with the shell 101 of the carrier member 105, the locking mechanism holding the guide sleeve 120 onto the syringe 205 can be activated or locked and the locking mechanism locking the guide sleeve 120 to the shell 101 can be deactivated or unlocked. The respective locking mechanisms can activate/deactivate in a simultaneous or step-wise manner. Once the switch in engagement occurs (i.e. locked engagement between the guide sleeve 120 and the shell 101 to an unlocked state and unlocked engagement of the syringe 205 and the guide sleeve 120 to a locked state), the syringe 205 can then be removed from the carrier member 105 with the guide sleeve 120 secured to the syringe 205. FIG. 6 shows an implementation of the system 100 with the syringe 205 inserted into the carrier 105. FIG. 7 shows an implementation of the system 100 after the syringe 205 has been used to fill the implant 110 and the syringe 205 has been decoupled from the carrier member 105. The guide sleeve 120 is shown detached from the carrier member 105 and is now attached to the syringe 205. It should be appreciated that unlocking or detaching the guide sleeve 120 from the carrier member 105 is not dependent upon filling the implant 110.

The locking mechanism between the shell 101 and the guide sleeve 120 can include one or more corresponding slots and tabs providing a fixed, but reversible coupling between the shell 101 and the guide sleeve 120. In one implementation and as best shown in FIGS. 3A-4B, 4A-4B, and 7, the guide sleeve 120 can include one or more slots 122 having a size and shape configured to accept tabs 405 of the shell 101 such that the tabs 405 reversibly insert through the slots 122 when the guide sleeve 120 is positioned within the central channel 103 of the shell 101. The slots 122 can be located on opposing sides of the guide sleeve 120. The guide sleeve 120 can also include one or more tabs 123 formed by a u-shaped slot 126 through a thickness of the guide sleeve 120. It should be appreciated that tabs 405 as well as tabs 123 can have a degree of flexibility such that they can move slightly with respect to the longitudinal axis A of the system to provide for reversible attachment between the guide sleeve 120 and the shell 101 as well as between the guide sleeve 120 and the syringe 205, which will be described in more detail below.

Figure 8A:
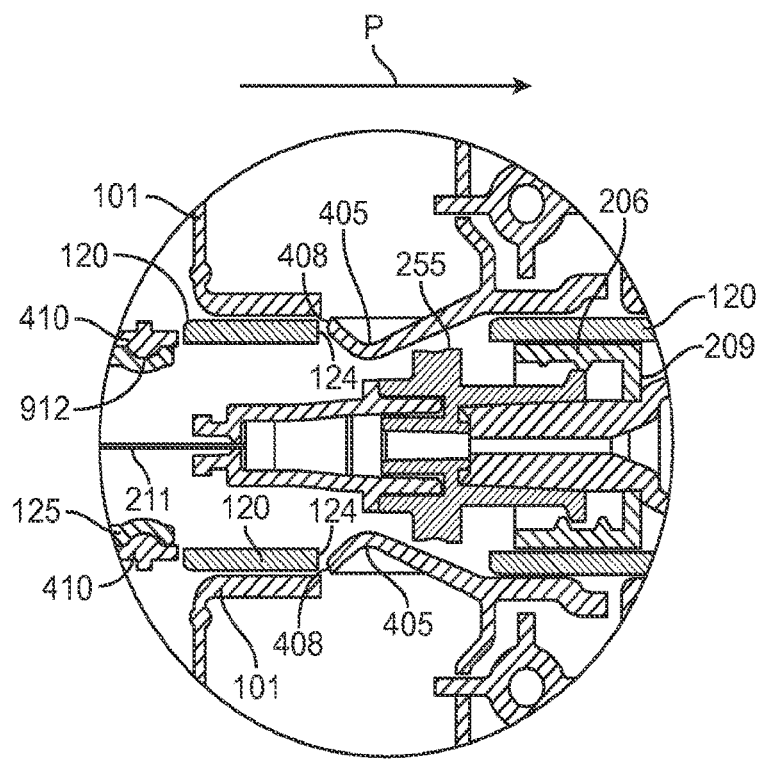
FIGS. 8A and 8B shows an example of a mechanism for locking a guide sleeve to a carrier member.
Figure 8B:
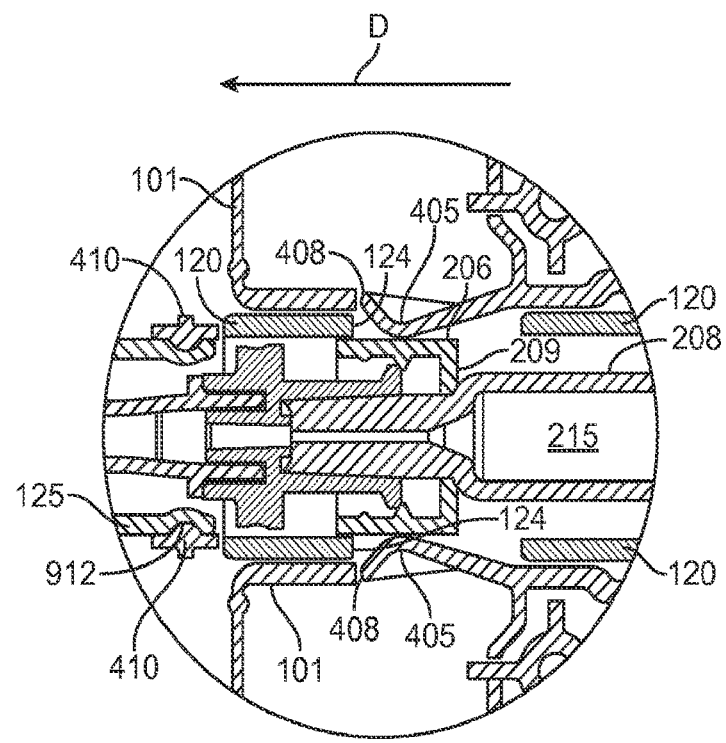

FIGS. 3A-3B, 4A-4B and also FIGS. 8A-8B show an implementation of a locking mechanism that initially locks the guide sleeve 120 to the shell 101 of the carrier member 105. The shell 101 can include one or more tabs 405 configured to insert through one or more corresponding slots 122 in the guide sleeve 120. In FIG. 8A, the tabs 405 are shown in a first state that locks the guide sleeve 120 to the shell 101 of the carrier member 105. The flexible tabs 405 can extend through the corresponding slots 122 in the guide sleeve 120 preventing withdrawal of the guide sleeve 120 in a proximal direction along arrow P. In the locked first state, an edge of the slot 122 can abut a distal edge of the tab 405. FIG. 8B shows a syringe 205 inserted distally into the guide sleeve 120 such that an outer surface of the needle assembly 210 of the syringe 205 presses against an inner surface of the flexible tabs 405 urging them in outward direction. The proximal end of the tabs 405 can be ramped such that the outer surface of the needle assembly 210 can smoothly press against and slide along the inner surface of the tabs 405 as the syringe 205 is urged in a distal direction along arrow D. The tabs 405 can be urged back out the slots 122 in the guide sleeve 120 releasing the locking engagement between the slots 122 of the guide sleeve 120 and the tabs 405 of the shell 101. In the unlocked second state, the edge 124 of the slot 122 may no longer abut the distal edge 408 of the tab 405.

This same act of inserting the syringe 205 distally through the guide sleeve 120 releasing the locked engagement between the guide sleeve 120 and the shell 101 can also cause the guide sleeve 120 to lock onto a portion of the syringe 205. In some implementations, the one or more tabs 123 formed by the u-shaped slot 126 through a thickness of the guide sleeve 120, for example, in the cylindrical underside of the guide sleeve 120 (see FIG. 4B and also FIG. 9). Similar to the tabs 405 of the shell 101, the tab 123 on the guide sleeve 120 can flex inward and outward relative to a longitudinal axis A of the guide sleeve 120 to capture a corresponding portion of the syringe 205. A free end 128 of the tab 123 can be angled or curved such that it projects inward towards the longitudinal axis of the guide sleeve 120, or have a feature that encroaches within the interior of the sleeve 120. When the syringe 205 is inserted distally through the guide sleeve 120 releasing the tabs 405 of the shell 101 from the slots 122 in the guide sleeve 120, the flexible tab 123 of the guide sleeve 120 can capture the corresponding portion of the syringe 205 preventing the syringe 205 from being detached from the carrier member 105 without the guide sleeve 120 being coupled to the syringe 205.

As mentioned previously, the guide sleeve 120 can include an inner diameter configured to receive the outer diameter of the syringe 205 such that the syringe 205 can be inserted through the guide sleeve 120 to inject drug into the implant 110 mounted within the implant holder 125 located distal to the guide sleeve 120 (see FIG. 9). The free end 128 of the flexible tab 123 of the guide sleeve 120 projecting inward towards the central longitudinal axis A of the system 100. The syringe 205 can urge the flexible tab 123 outward away from the central longitudinal axis A as the syringe 205 is inserted through the guide sleeve 120. Thus, the syringe 205 can be freely inserted in a distal direction along arrow D through the guide sleeve 120. However, the tab 123 can prevent the syringe 205 from being withdrawn in a proximal direction along arrow P away from the guide sleeve 120. As best shown in FIG. 9, a distal region of the syringe 205 can include a first portion 206 having a first outer diameter and a second portion 208 having a second outer diameter. The first portion 206 can be located distally to the second portion 208 and the first outer diameter can be larger than the second outer diameter. As the syringe 205 is inserted through the guide sleeve 120, the outer diameter of the first portion 206 can abut the free end 128 of the tab 123 urging the tab 123 outward. Once the first portion 206 is advanced distal to the tab 123, the free end 128 can flex back inward towards the longitudinal axis A and towards the smaller diameter second portion 208 located proximal to the first portion 206. The first portion 206 can have a proximal ledge 209 such that if the syringe 205 is withdrawn in a proximal direction, the free end 128 of the tab 123 can abut the proximal ledge 209 and cause the now-released guide sleeve 120 to withdraw along with the syringe 205.

As mentioned above, an implant holder 125 can be removably attached within at least a region of the central channel 103 of the shell 101. The implant holder 125 can be positioned such that an interior 901 of the implant holder 125 is coaxial with the central channel 103 of the carrier member 105 and the guide sleeve 120 (see FIG. 2A). A proximal end 902 of the implant holder 125 can lie adjacent to the distal end of the guide sleeve 120 and a distal end 903 of the implant holder 125 can extend beyond the central channel 103 into the window 111. The interior 901 of the implant holder 125 can be configured to receive at least a portion of the needle assembly 210 of the syringe 205 (see FIG. 6), as will be described in more detail below.

Figure 10C:
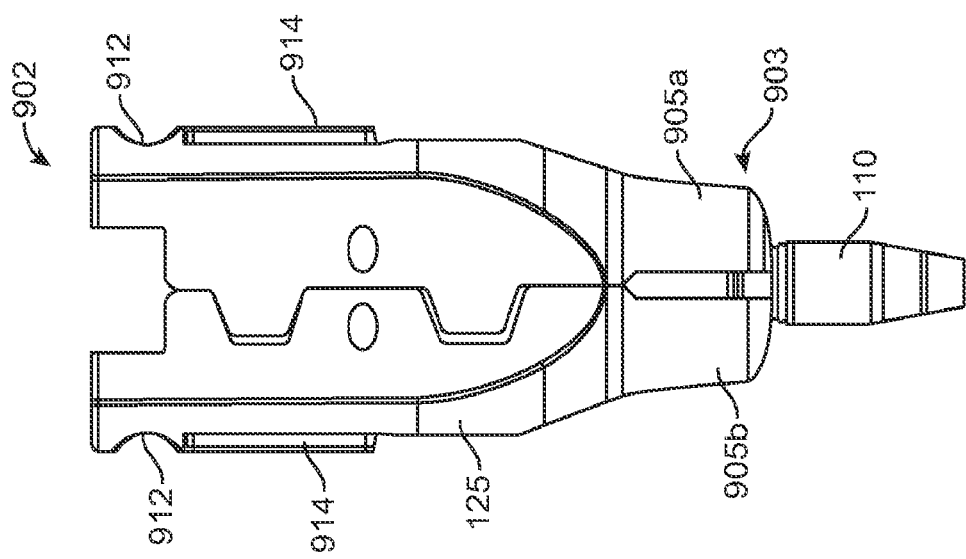
FIGS. 10C, 10D, and 10E are front, side and back views, respectively of the implant holder of FIG. 10B.
Figure 10D:
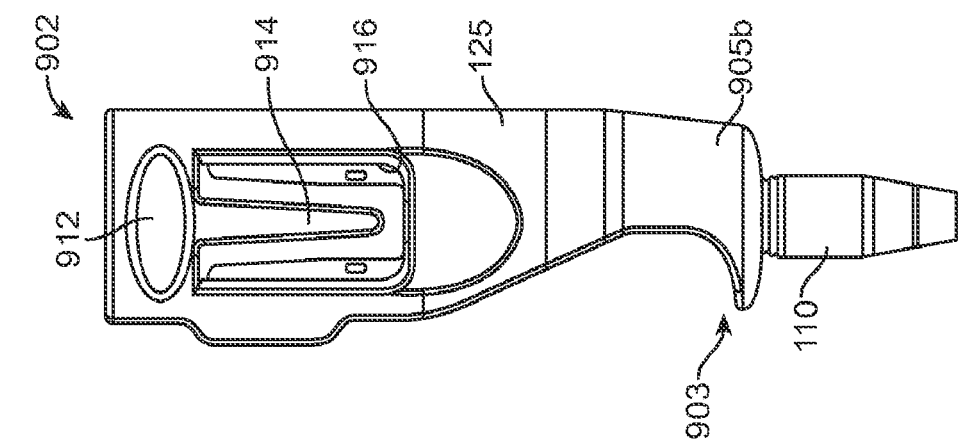
Figure 10E:
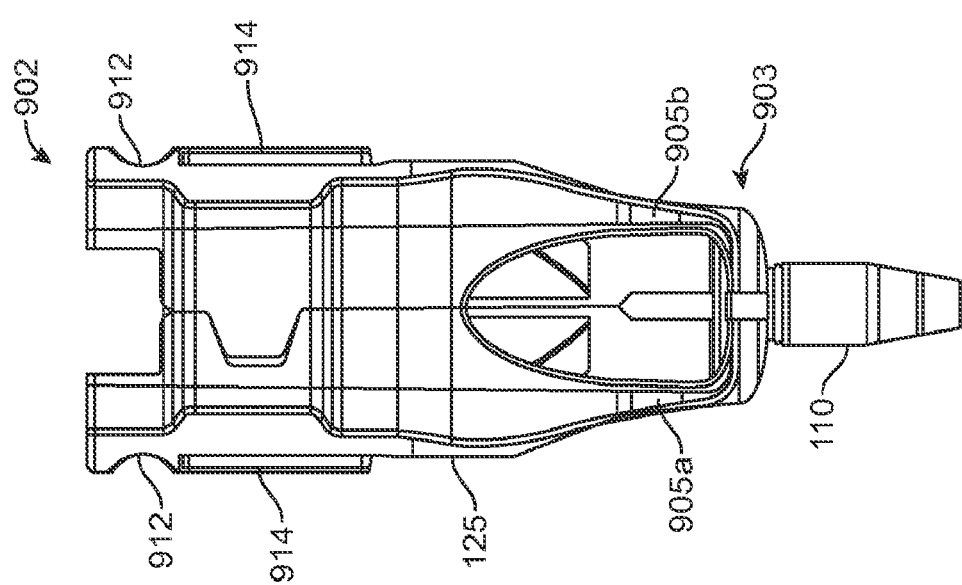
Figure 10G:
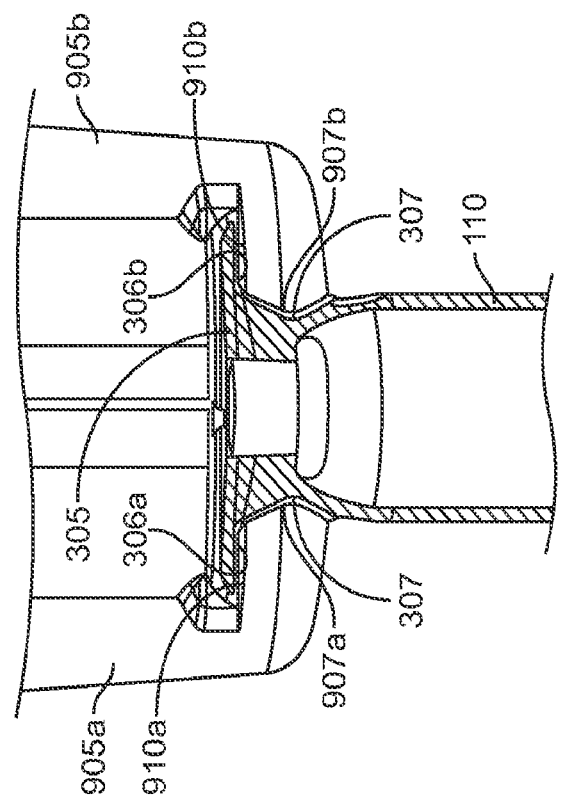
FIG. 10G is a detail view of FIG. 10F taken along circle G.
Figure 10F:
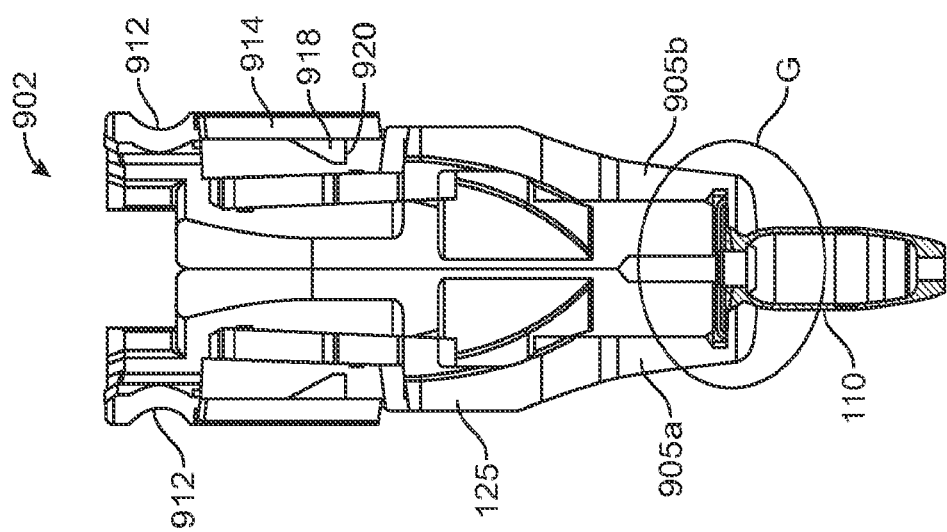
FIG. 10F is a partial cross-sectional view of the implant holder of FIG. 10B.

Now with respect to FIGS. 10A-10G, the implant holder 125 can include a pair of moveable mating graspers 905a, 905b configured to releasably secure the implant 110 to the carrier member 105. As best shown in FIGS. 10F and 10G, the implant 110 can include a proximal retention structure 305 that can include an indentation 307 dimensioned to receive first protrusion 907a of a first grasper 905a and a second protrusion 907b of a second grasper 905b to hold the implant 110 therebetween. The protrusions 907a, 907b can be shaped in a variety of ways to engage the implant 110, including lentoid, oval, elliptical, or circular structures. The protrusions 907a, 907b can include a structure similar to the shape profile or outer contour or corresponding geometry of the indentation of the implant 110.

Still with respect to FIGS. 10F-10G, first protrusion 907a on the first grasper 905a can include a proximal surface 910a to engage a region of the distal surface 306a of the retention structure 305, and the second protrusion 907b on the second grasper 905b can include a proximal surface 910b to engage another region of the distal surface 306b of the retention structure 305. The first grasper 905a can be urged toward the second grasper 905b to slide the first protrusion 907a and the second protrusion 907b into the indentation 307 of the retention structure 305 such that the proximal surfaces 910a, 910b engage the distal surfaces 306a, 306b. The graspers 905a, 905b can extend substantially around a portion of the retention structure 305 of the implant 110 to hold the implant 110. The septum or fill port of the implant 110 can be available within the interior 901 of the implant holder 125 and the body of the implant 110 can extend beyond the implant holder 125. The implant 110 can be held by the implant holder 125 such that a longitudinal axis of the implant 110 is aligned substantially concentric or coaxial with the longitudinal axis A of the system 100.

The syringe needle 211 can be inserted coaxially along the axis A of the implant 110 such that the needle 211 of the syringe 205 is advanced along the axis A toward the proximal end of the implant 110. The needle 211 of the syringe 205 can penetrate the fill port until a needle stop 212 contacts the proximal surface 910 of the graspers 905 or a proximal end of the implant 110 preventing further penetration of the needle 211. The interior 901 of the implant holder 125 as well as the guide sleeve 120 can further aid in aligning the syringe 205 and the needle 211 with the implant 110 and with the longitudinal axis A. The implant holder 125 can additionally incorporate an opening into the interior 901 such that a needle can be inserted at an angle to the longitudinal axis A.

Figure 13:
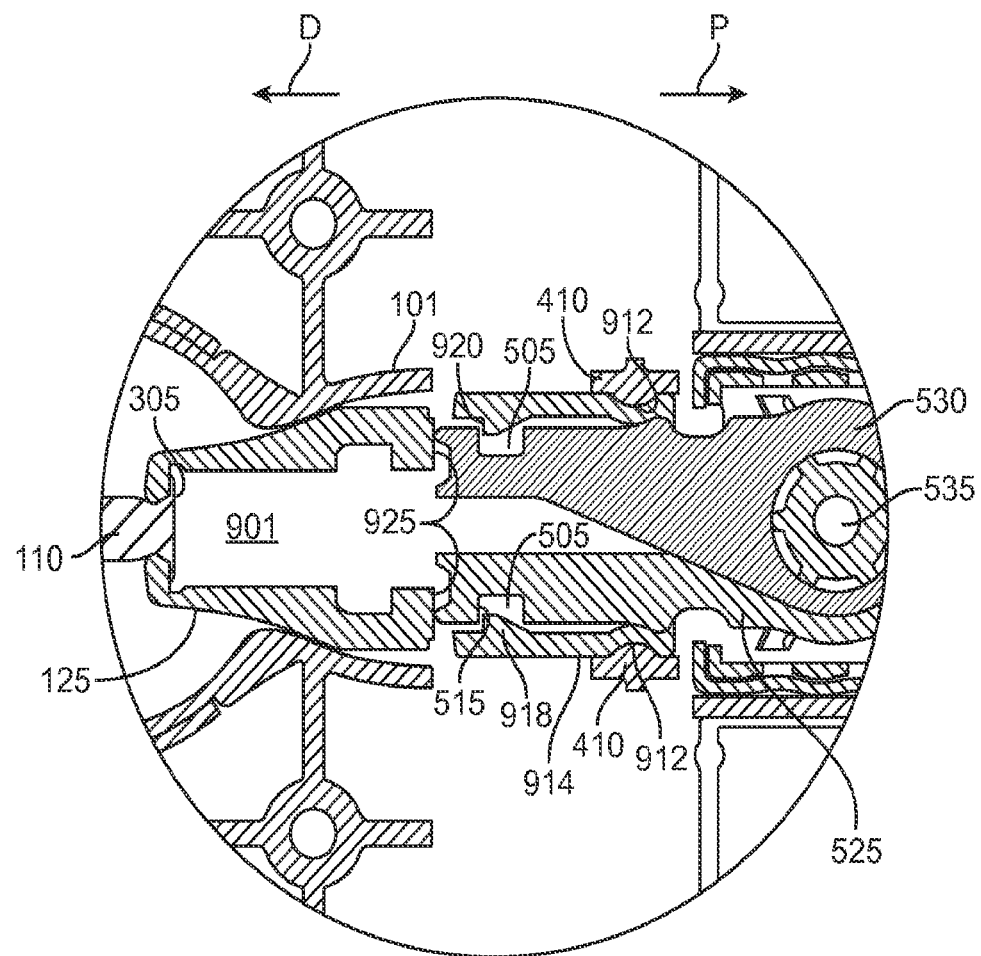
FIG. 13 shows a locking mechanism that initially secures the implant holder to the carrier member.

The implant holder 125 can be an interchangeable element that can lock in an alternating fashion with different portions of the system 100, such as the shell 101 of the carrier 105 and a portion of the handle member 115. The proximal end 902 of the implant holder 125 can be reversibly coupled to a region of the shell 101 such as within the central channel 103 by a locking mechanism. The locking mechanism can be configured to unlock the implant holder 125 from the shell 101 and then lock the implant holder 125 onto the handle member 115 once the handle member 115 is inserted into the carrier member 105, which is described in more detail below. The implant holder 125 can be attached to the region of the shell 101 and then attached to the handle member 115 upon release from the shell 101. The locking mechanism can include an indentation 912 near a proximal end 902 of the implant holder 125 configured to receive a correspondingly shaped element 410 of the shell 101 (see FIG. 3A and also FIG. 13). The indentation 912 can have smooth edges such that the implant holder 125 can be removed from the element 410, as will be described in more detail below. The locking mechanism can also include a tab 914 formed by a u-shaped slot 916 located adjacent the indentation 912, such as just distal to the indentation 912. The tab 914 can include a projection 918 on its inner surface (see FIG. 10F) configured to engage with a correspondingly shaped recess 505 within a region of the handle member 115 when the handle member 115 is inserted through the interior 901 of the implant holder 125 as will be described in more detail below.

Figure 11:
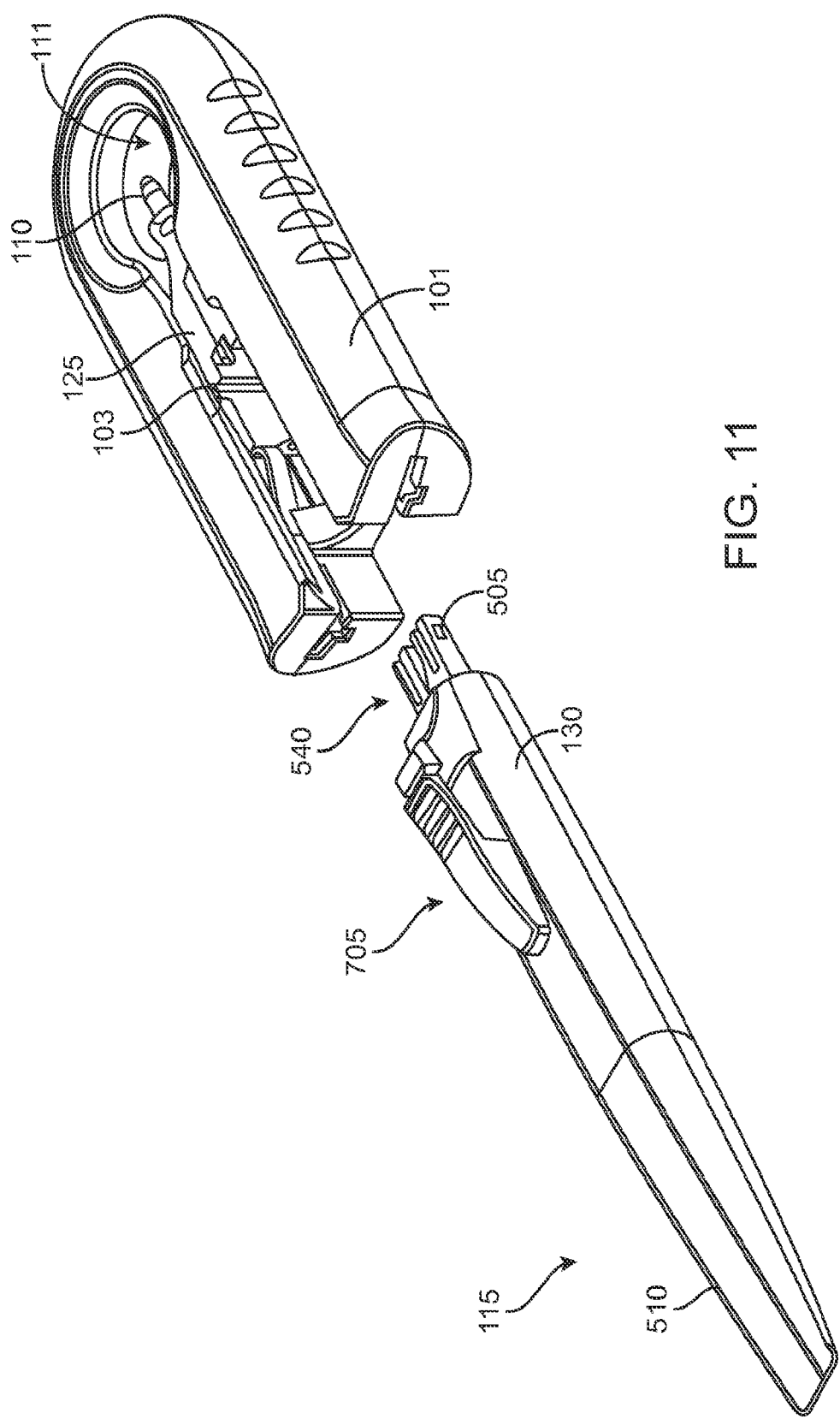
FIG. 11 shows a handle member of the system ready to be inserted into the carrier member.

As mentioned above, the system 100 can also include the handle member 115. After the syringe 205 is removed from the carrier 105 and the guide sleeve 120 has transferred attachment from the shell 101 of the carrier 105 to the syringe 205 as shown in FIG. 7, the handle member 115 can be attached to the implant holder 125 holding the implant 110 (see FIGS. 11 and 12). The implant holder 125 can be interchangeably attached to the shell 101 of the carrier 105 and the handle member 115. Insertion of the handle member 115 into the carrier member 105 can release the attachment of the implant holder 125 with the shell 101 and cause the attachment between the implant holder 125 and the handle member 115 such that the implant holder 125 can be removed from the carrier 105 and the handle member 115 can be used to insert the implant being held by the implant holder 125 into a patient.

Figure 12:
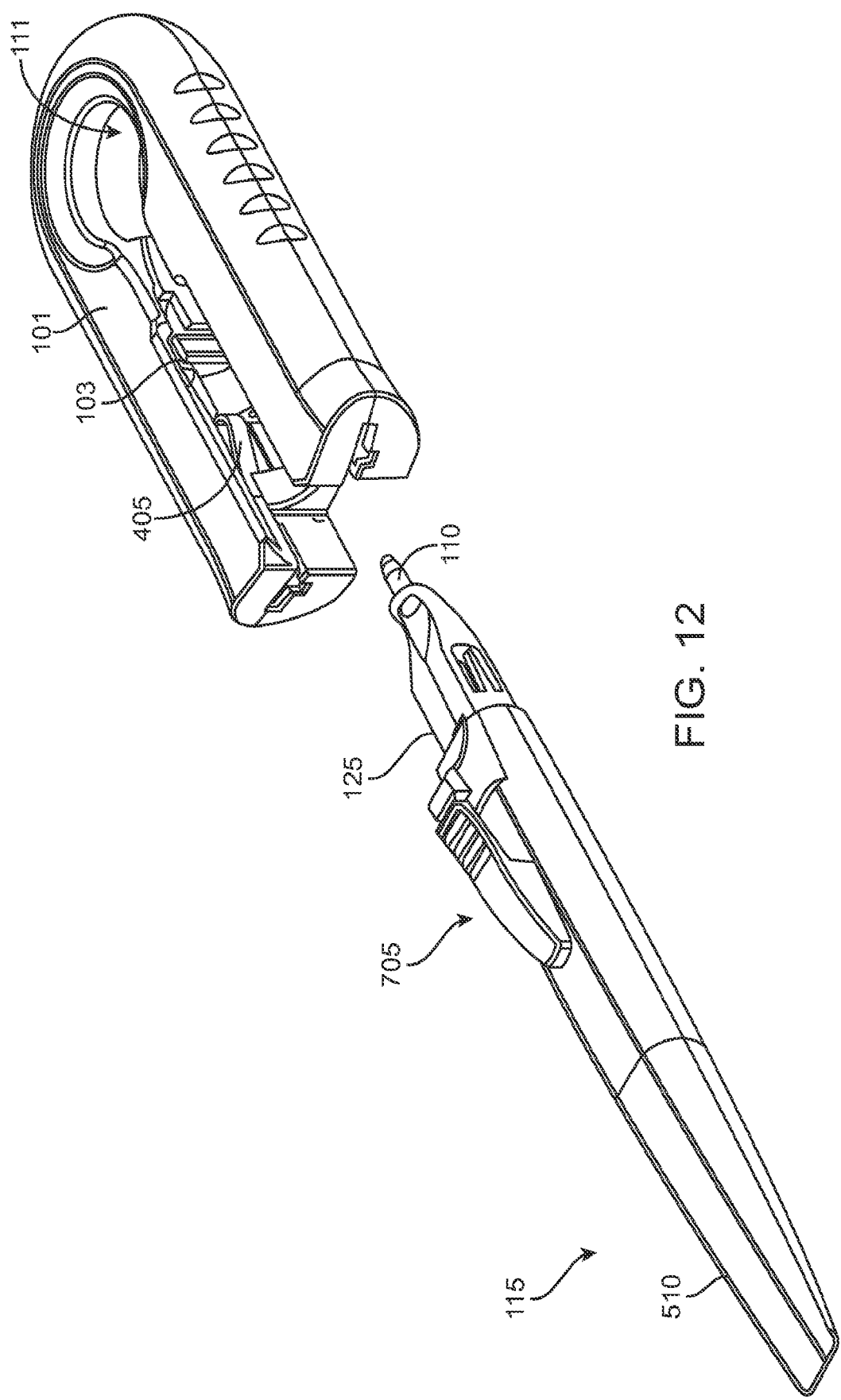
FIG. 12 shows the handle member after it has been removed from the carrier member with the removable implant holder now attached to the handle member.

The handle member 115 can include an elongated proximal portion 510 that can be grasped by a user and the distal attachment portion 130 that can releaseably attached to the implant 110 via the implant holder 125. The proximal portion 510 of the handle member 115 can be sized and shaped to be grasped by a user and can have an ergonomic shape that facilitates quick and easy positioning of the implant 110 and release of the implant 110 into the patient. The distal attachment portion 130 of the handle member 115 can be inserted into the central channel 103 of the carrier member 105 after removal of the guide sleeve 120 from the central channel 103. In this regard, the attachment portion 130 can removably attach, engage or otherwise mate with the implant holder 125 of the carrier member 105, which holds the implant 110 (see FIG. 11). Once attached to the implant holder 125, the handle member 115 can be removed from the carrier member 105 such that it takes the implant holder 125 (and attached implant 110) out of the carrier member 105 along with it. The handle member 115 can then be used to manipulate the implant 110 held by the implant holder 125 such that the implant 110 can be inserted into an eye. FIG. 12 shows handle member 115 after it has been removed from the carrier member 105 with the removable implant holder 125 now attached to the handle member 115.

As described above and with respect to FIG. 13, the proximal end 902 of the implant holder 125 can be reversibly coupled to a region of the shell 101 by a locking mechanism configured to unlock the implant holder 125 from the shell 101 and lock the implant holder 125 onto the handle member 115 once the handle member 115 is inserted into the carrier member 105. The locking mechanism can include the indentation 912 located near a proximal end 910 of each grasper 905 and the tab 914 adjacent the indentation 912 having the projection 918 on its inner surface. The projection 918 can have a ramped proximal end and a flat lower surface 920. When the implant holder 125 is locked to the shell 101, the correspondingly-shaped element 410 of the shell 101 can rest within the indentation 912. When the attachment portion 130 of the handle 115 is inserted through the implant holder 125, the projection 918 on the inner surface of the tab 914 can insert within the recess 505 near the distal end of the attachment portion 130. Distal movement of the attachment portion 130 along arrow D through the interior 901 of the implant holder 125 can cause the tab 914 to flex slightly outward as the outer surface of the distal end of the attachment portion 130 slides past the ramped surface of the projection 918 on the inner surface of the tab 914. Once the projection 918 aligns with the recess 505, the tab 914 can flex back inward such that the projection 918 snaps into the recess 505. The recess 505 and the projection 918 can have corresponding shapes such that the projection 918 can be received at least in part within the recess 505. Further distal movement of the handle 115 through the interior 901 of the implant holder 125 can be prevented due to contact between the distal-most end of the attachment portion 130 and a surface 925 of the interior 901 of the implant holder 125. Thus, a region of the attachment portion 130 between the recess 505 and the distal-most end of the attachment portion 130 can be captured between the projection 918 and this surface 925 (see FIG. 13). Proximal withdrawal of the handle 115 along arrow P from the central channel 103 of the shell 101 can cause a lower surface 920 of the projection 918 to abut a distal wall 515 of the recess 505 causing the implant holder 125 to be withdrawn with the handle 115 in a proximal direction along arrow P out from the central channel 103.

Figure 14A:
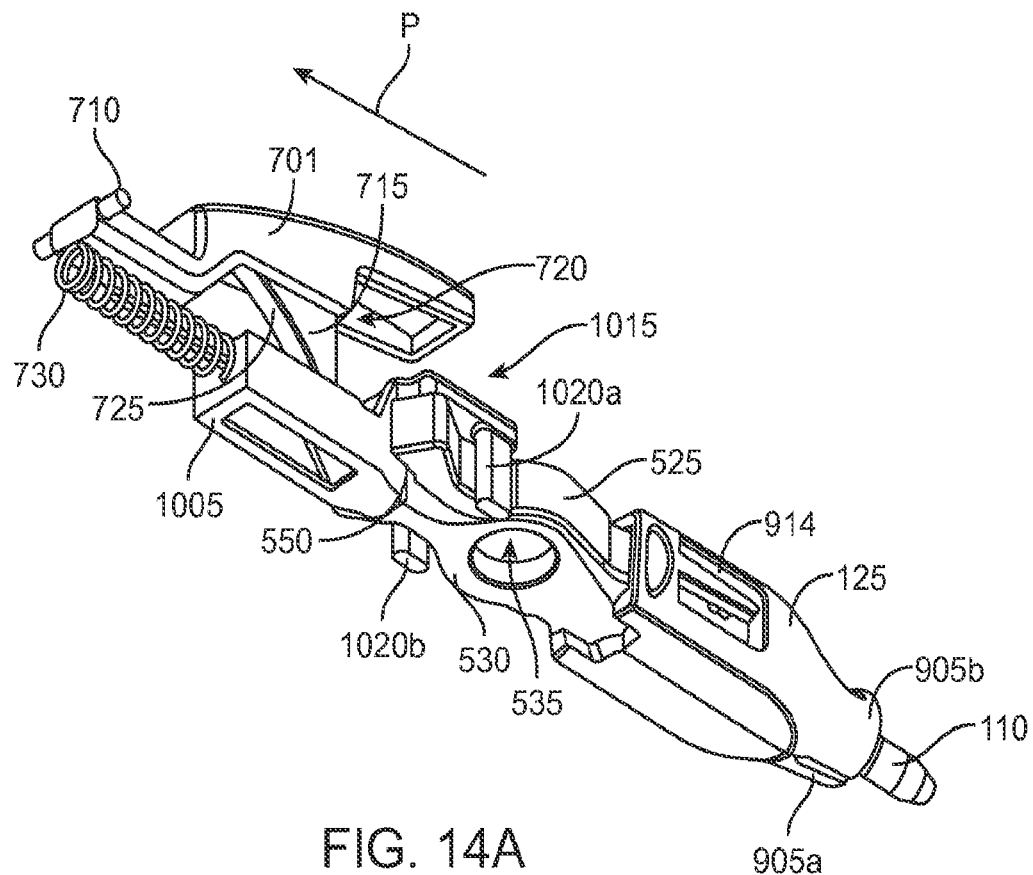
FIGS. 14A and 14B show the implant holder in a grasping state and a released state, respectively.
Figure 14B:
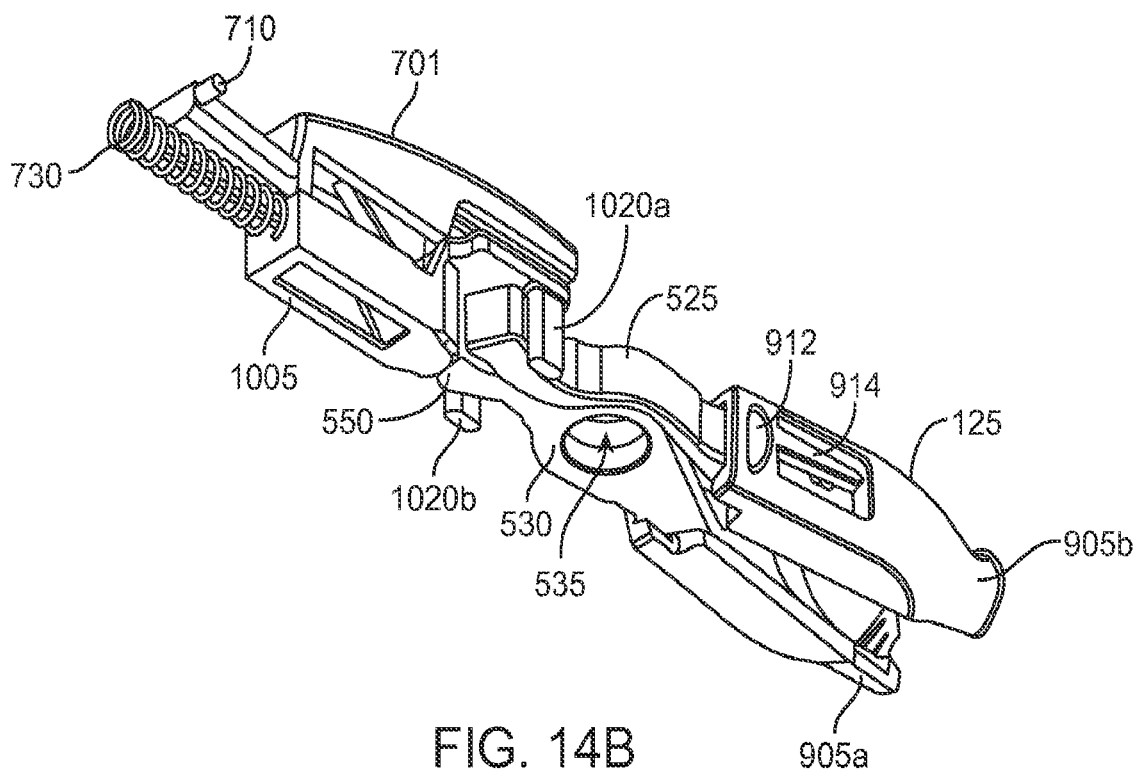
Figure 14C:
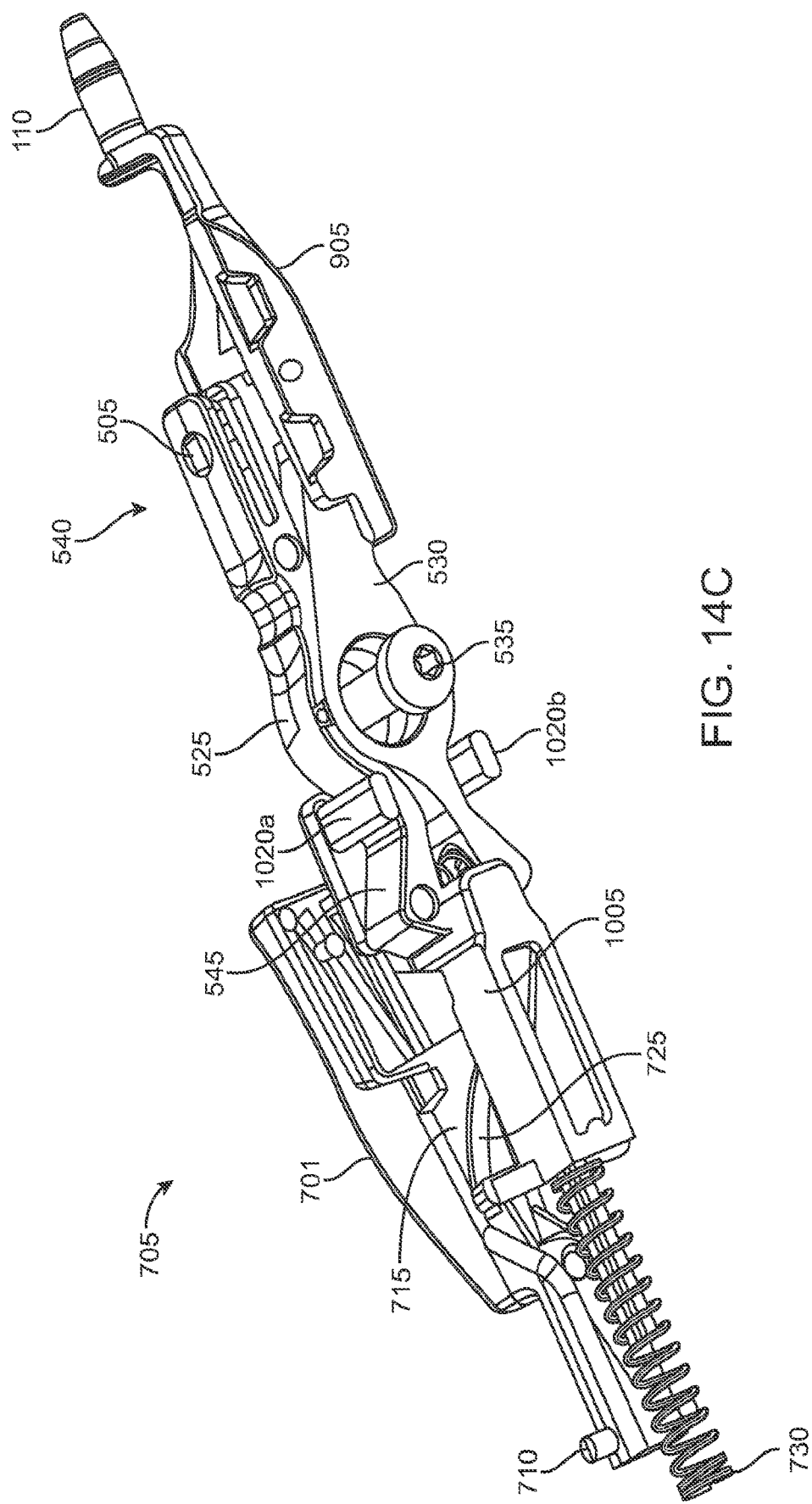
FIGS. 14C and 14D are partial views of the actuator system of the handle member.
Figure 14D:
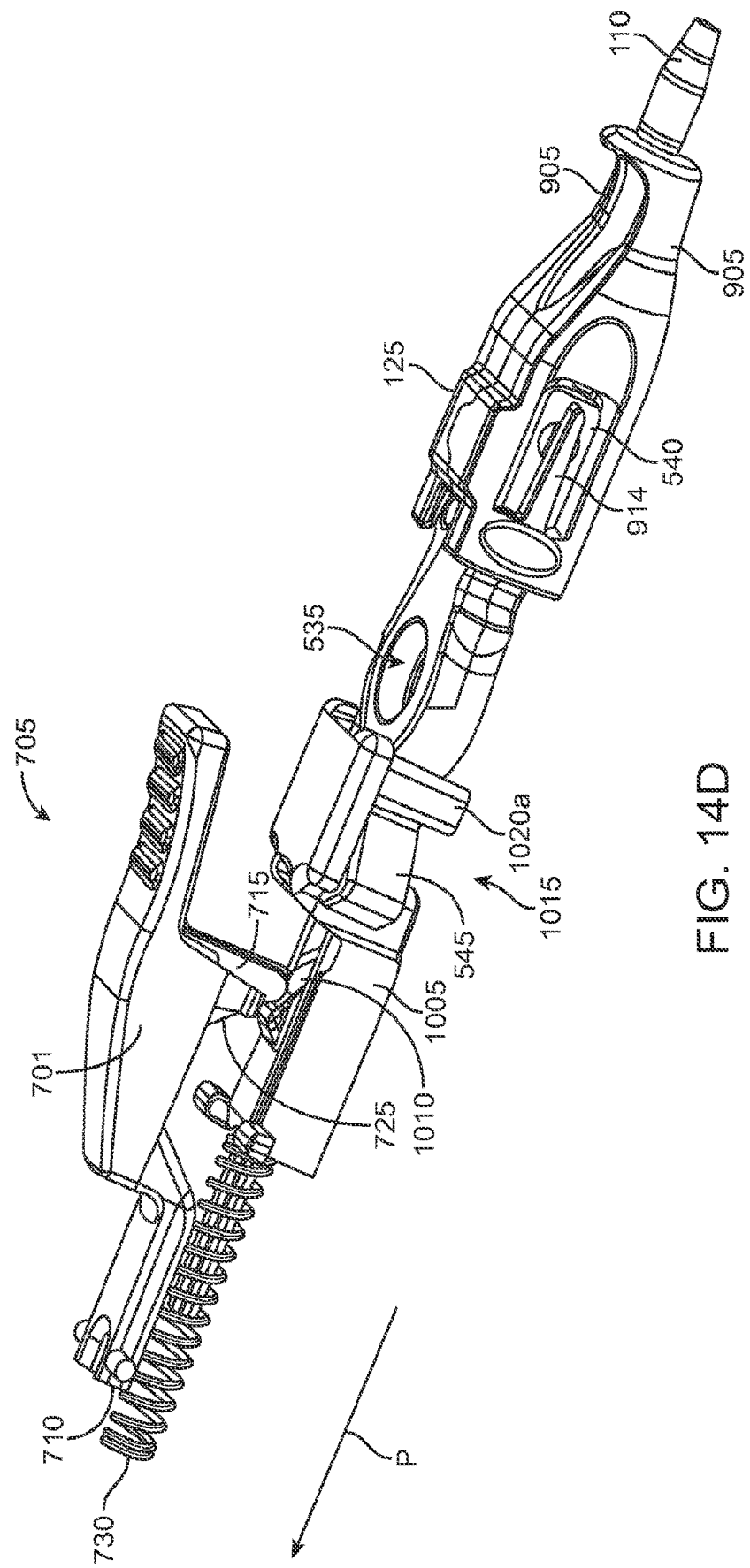
Figure 15A:
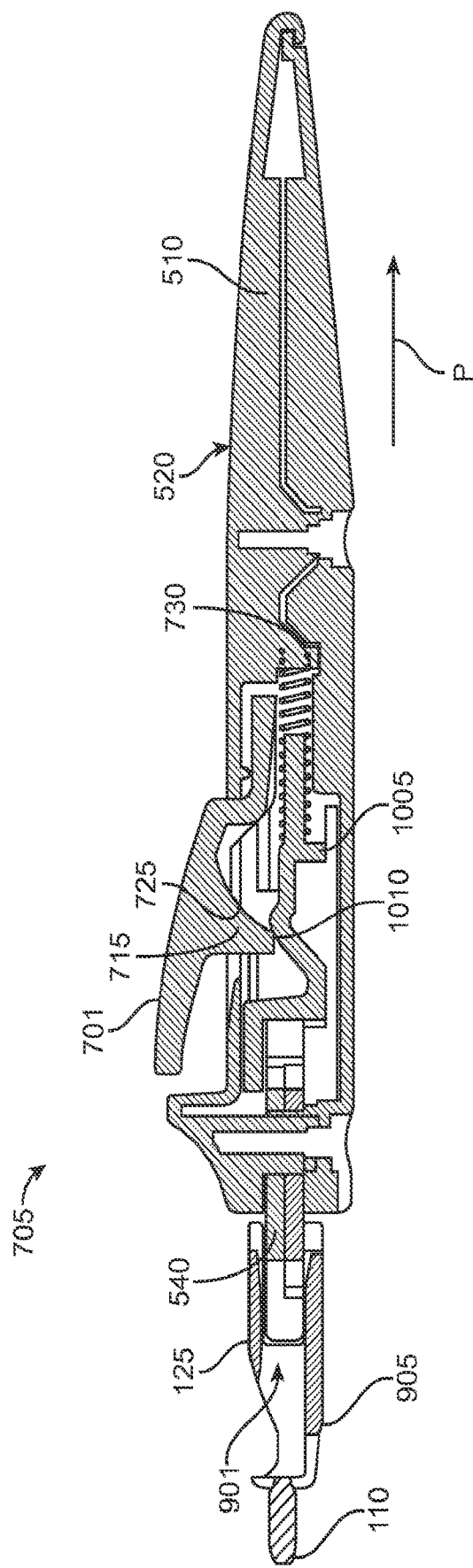
FIGS. 15A and 15B are cross-sectional views of a mechanism for releasing the implant from the implant holder.
Figure 15B:
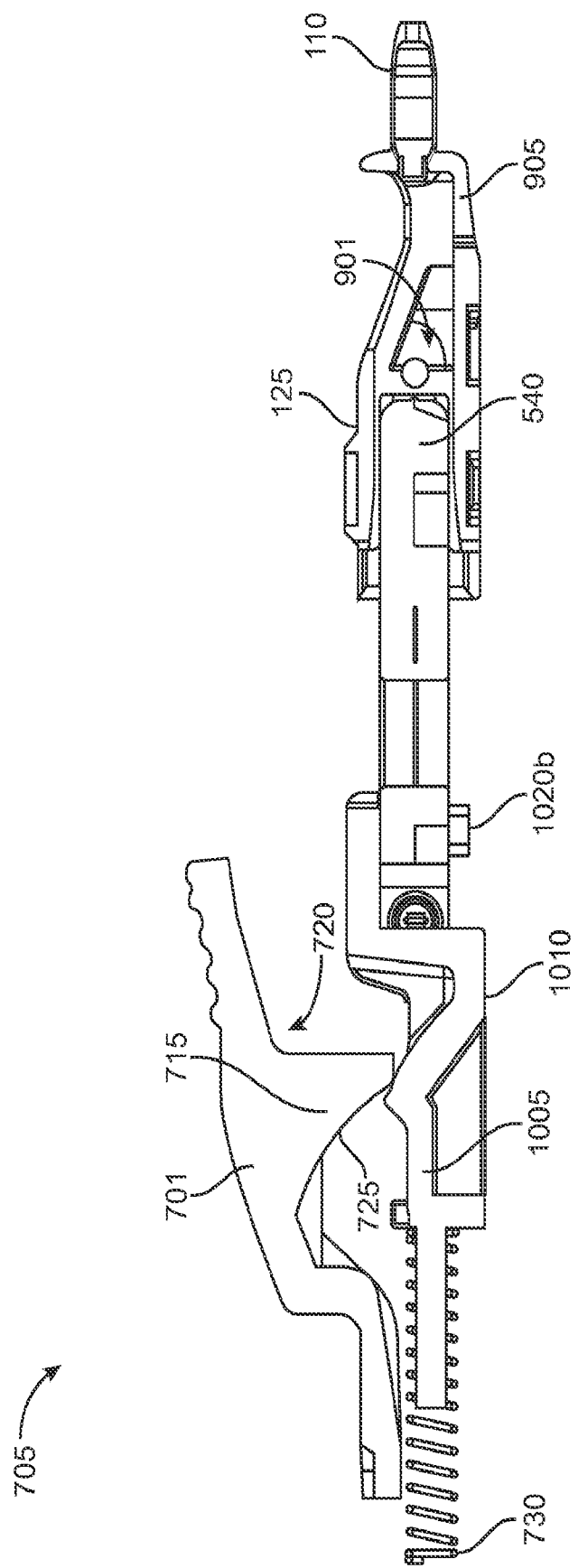

Now with regard to FIGS. 14A-14D, the handle member 115 can have at least one deployment mechanism including an actuator 705, such as a button, knob, slider, etc., that can be actuated to detach the implant 110 from the implant holder 125 and handle member 115. The actuation of the actuator 705 can simply release the implant 110 or it can push or otherwise expel the implant 110 from the handle member 115. FIGS. 14A and 14B shows an implementation of a deployment mechanism that releases the implant 110 from the handle member 115 upon actuation of the actuator 705. As described above, the implant holder 125 can include a pair of movable tips or graspers 905 that grasp the implant 110 such that when the handle member 115 is inserted within the interior 901 of the implant holder 125 the graspers 905 secure the implant 110 to the handle member 115. In the initial state shown in FIG. 14A, the graspers 905 can be positioned such that they hold the implant 110 in a secured position relative to the handle member 115. Once the actuator 705 is depressed, the graspers 905 can separate and release the implant 110 as shown in FIG. 14B. FIG. 15A-15B show cross-sectional views of an implementation of the deployment mechanism. The actuator 705 can be pressed (or slide) so as to exert a force onto a spring held slider member 1005. The force of the actuator 705 can slide the slide member 1005 to a position that causes the graspers 905 to open. The amount of force required to slide the slider member 1005 forward and open the graspers 905 can be variable. The slider member 1005 and the actuator interface at ramped connection can have different ramp angles resulting in a smoothing of the force required for the user to open the handle tips.

In an implementation, the actuator 705 can include an actuator element 701 configured to pivot around a pivot pin 710 when the actuator 705 is depressed towards an upper surface 520 of the handle member 115. The actuator element 701 can also include a projection 715 extending from its lower surface 720 such that as the element 701 pivots around the pivot pin 710 the projection 715 is moved downwards such that the ramped surface 725 of the projection 715 slides along a ramped surface 1010 of the slider member 1005. This contact between the ramped surface 725 of the projection 715 against the ramped surface 1010 of the slider member 1005 can cause the slider member 1005 to move in a proximal direction against the force of the spring 730 compressing the spring 730. The slider member 1005 can have a forked region 1015 near its distal end. The attachment portion 130 of the handle member 115 can interface with the forked region 1015. The attachment portion 130 can include a first arm 525 rotatably coupled to a second arm 530 around a pivot point 535. The first arm 525 and second arm 530 can be biased such as by a spring or other element such that their distal ends 540 are urged towards one another. As described above, the distal region 540 of the arms 525, 530 can extend within the interior 901 of the implant holder 125 such that the projections 918 of the implant holder 125 mate with the recesses 505 on the arms 525, 530. A region 545 of the arms 525, 530 proximal of the pivot point 535 can interface with the forked region 1015 of the slider member 1005. A first prong 1020a of the forked region 1015 can rest against a first region 550 of the arm 525 and a second prong 1020b of the forked region 1015 can rest against a second region 550 of the arm 530 (see FIG. 14A). When the slider member 1005 is moved in a proximal direction along arrow P, the first and second prongs 1020a, 1020b can slide relative to the arms 525, 530 such that they abut a ramped proximal end 545 of each respective arm 525, 530 and cause the arms 525, 530 to open or pivot relative to one another around pivot point 535. The distal region 540 of the arms 525, 530 can move away from one another in a scissor-like movement. This, in turn, can cause the distal region 540 of the arms 525, 530 engaged with the projections 918 of the implant holder 125 to press against the inner surface of the implant holder 125 and can cause the graspers 905 to likewise move away from one another releasing the implant 110 held therebetween (see FIG. 14B).

The actuator element 701 can be arranged relative to the arms 525, 530 of the handle member 115 such that as the actuator element 701 is pressed downwards towards the upper surface of the handle member 115, the arms 525, 530 can each move outward at an angle away from the longitudinal axis A of the system 100 and from one another. The arms 525, 530 can be configured to move away from one another such that one arm moves to a first side and the opposing arm moves to a second opposite side away from the longitudinal axis A of the system 100. The arms 525, 530 also can be configured to move away from one another such that one arm moves upwards and one arm moves downwards away from the longitudinal axis A of the system 100. As mentioned previously, reference herein to terms such as "upper," "lower," "upwards," "downwards," "front," "back," "proximal," "distal" etc. are used herein for orientation from one point of view of a user operating the systems described herein and are not intended to be limiting. For example, the actuator element 701 can be positioned on an upper surface of the handle member 115 from the point of view of the user such that the actuator element 701 is pressed using a thumb and the actuator element 701 moved towards the upper surface of the handle member 115. The actuator element 701 also can be positioned on a lower surface of the handle member 115 from the point of view of the user such that the actuator element 701 is pressed using a finger and the actuator element 701 moved towards the lower surface of the handle member 115.

One or more components of the system 100 can be provided as a kit. The kit can include sterile packaging within which one or more components of the system 100 can be contained including the carrier member 105 having a guide sleeve 120 and implant holder 125 attached. An implant 110 can be held within the implant holder 125 or the implant 110 can be contained within sterile packaging separated from the system 100 such that the implant 110 is engaged with the implant holder 125 after the sterile kit has been opened. The kit can further include a handle member 115. The kit can further include needle assembly 210 configured to couple to a pre-filled syringe. Alternatively, the kit can include the syringe. The kit can further include a removal tool. In some implementations, the kit can include a carrier member 105 having a guide sleeve 120 and having an implant holder 125 coupled to the shell 101 of the carrier member 105. The implant holder 125 can be reversibly coupled to an implant 110. The implant 110 can be empty. In an interrelated implementation, the kit can further include a handle member 115 configured to engage with the implant holder 125 holding the implant 110 after the implant 110 has been filed with a drug. In an interrelated implementation, a syringe 205 can be provided that is configured to interdigitate with a portion of a carrier member 105 such that a needle of the syringe 205 can insert through a proximal portion of the implant 110 being held by the carrier member 105 to fill the implant 110 with a drug. The syringe 205 can be pre-filled with one or more therapeutic agents. The carrier member 105 can include a guide sleeve 120 configured to lock onto a portion of the syringe 205 upon insertion of the syringe 205 into the guide sleeve 120 of the carrier member 105. The implant 110 can be held by an implant holder 125 locked onto the carrier member 105, such as within the central channel 103. The implant holder 125 holding the implant 110 can attach to a portion of a handle member 115 after removal of the syringe 205 from the carrier member 105 upon filling of the implant 110. The handle member 115 having the implant holder 125 now attached to it can be used to deliver the implant 110 held within the implant holder 125 into a target location of the patient. In an interrelated implementation, the kit can include a carrier member 105 having a shell 101 and a guide sleeve 120, and an implant holder 125 holding an implant 110. The carrier member 105 can have a central channel 103 that facilitates access to the implant 110 being held by the implant holder 125, such as for filling with a syringe 205. The syringe 205 can be part of the kit or a separate component. The syringe 205 can be pre-filled with one or more therapeutic agents or can be empty. The handle member 115 can also be part of the kit or a separate component. The implant 110 can be part of the kit or a separate component. In an interrelated aspect, all of the components can be provided as a single kit or can be provided as separate components.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed:

1. An ocular implant handling system, comprising:
    a carrier member comprising:
        a shell having a central channel extending at least partially through the shell from a proximal end towards a distal end of the shell;
        a guide sleeve removably attached within at least a first region of the central channel of the shell, the guide sleeve defining a proximal port into the central channel that is accessible from the proximal end of the shell; and
        an implant holder removably attached within at least a second region of the central channel of the shell adjacent to a distal end of the guide sleeve, the implant holder having a pair of graspers adapted to releasably secure an implant at a distal end of the implant holder; and
    a handle member usable for inserting the implant into an eye.

2. The system of claim 1, wherein the handle member further comprises an actuator configured to detach the implant from the implant holder.

3. The system of claim 2, wherein when the actuator is in a first state, the graspers are positioned adjacent one another and surround the implant.

4. The system of claim 2, wherein when the actuator is in a second state, the pair of graspers are urged away from one another and release the implant.

5. The system of claim 2, wherein the actuator comprises an actuator element, a spring-held slider member, and a pair of arms.

6. The system of claim 5, wherein the actuator element has a projection extending from a lower surface and having a ramped surface.

7. The system of claim 6, wherein movement of the actuator element towards an upper surface of the handle causes the ramped surface to slide against a corresponding ramped surface of the slider member urging the slider member in a proximal direction relative to the pair of arms.

8. The system of claim 7, wherein the slider member has a forked region interfaced with the pair of arms such that proximal movement of the slider member causes the pair of arms to open in a scissor-like movement.

9. The system of claim 8, wherein opening the pair of arms urges the pair of graspers away from one another releasing the implant held therebetween.

10. The system of claim 1, further comprising a fill syringe sized and shaped to be inserted through the port into the central channel through the guide sleeve.

11. The system of claim 10, wherein the handle member comprises an elongated proximal portion and a distal attachment portion.

12. The system of claim 11, wherein the distal attachment portion releasably attaches to the implant holder.

13. The system of claim 11, wherein the distal attachment portion of the handle member is sized and shaped to be inserted through the central channel after the fill syringe and the guide sleeve coupled to the fill syringe are removed from the shell.

14. The system of claim 11, wherein the distal attachment portion comprises a first arm and a second arm.

15. The system of claim 10, wherein the guide sleeve simultaneously detaches from the shell and attaches to the fill syringe when the fill syringe is inserted into the central channel.

16. The system of claim 10, wherein the fill syringe has a first portion having a first outer diameter and a second portion having a second outer diameter, wherein the first portion is located distal to the second portion and the first outer diameter is larger than the second outer diameter.

17. The system of claim 16, wherein distal advancement of the fill syringe through the guide sleeve causes the first portion of the fill syringe to abut against a free end of a guide sleeve tab and urges the guide sleeve tab outward away from a longitudinal axis of the guide sleeve.

18. The system of claim 17, wherein further distal advancement of the fill syringe through the guide sleeve advances the first portion to a position that is distal to the free end of the guide sleeve tab such that the free end flexes back inward toward the longitudinal axis and towards the second outer diameter of the second portion located proximal to the first portion.

19. The system of claim 18, wherein the free end of the guide sleeve tab abuts a proximal ledge of the first portion locking the guide sleeve to the fill syringe.

20. The system of claim 19, wherein the implant holder has an interior configured to receive at least a portion of a needle assembly of the fill syringe.

21. The system of claim 20, wherein the pair of graspers extend substantially around a retention structure of the implant such that a fill port of the implant is available from within the interior of the implant holder.

22. The system of claim 21, wherein a first grasper of the pair of graspers has a first protrusion and a second grasper of the pair of graspers has a second protrusion, wherein the first and second protrusions are configured to be received within an indentation distal to the retention structure of the implant such that the retention structure is held within the interior of the implant holder and a reservoir extends distal to the implant holder.

23. The system of claim 10, wherein the fill syringe has a needle assembly having an outer surface.

24. The system of claim 23, wherein insertion of the fill syringe through the guide sleeve positioned within the central channel causes contact between the outer surface of the needle assembly and an inner surface of a shell tab urging the shell tab to flex outward away from the guide sleeve slot into an unlocked second state wherein an edge of the guide sleeve slot no longer abuts a distal end of the shell tab.

25. The system of claim 1, wherein the implant holder is configured to interchangeably couple with the carrier member and the handle member.

* * * * *